United States Patent
van de Wiel et al.

(10) Patent No.: US 6,183,987 B1
(45) Date of Patent: *Feb. 6, 2001

(54) PRODUCTION OF BIOLOGICALLY ACTIVE RECOMBINANT BOVINE FOLLICLE STIMULATION HORMONE (REC BFSH) IN THE BACULOVIRUS EXPRESSION SYSTEM

(75) Inventors: Dirk Franciscus Marinus van de Wiel, Harderwijk; Petrus Antonius van Rijn, Lelystad; Robertus Jacobus Maria Moormann, Dronten; Robert Hans Meloen, Lelystad, all of (NL)

(73) Assignee: Stichting Instituut voor Dierhouderij en Diergezonheld, Lelystad (NL)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/894,402
(22) PCT Filed: Feb. 16, 1996
(86) PCT No.: PCT/NL96/00073
§ 371 Date: Nov. 12, 1997
§ 102(e) Date: Nov. 12, 1997
(87) PCT Pub. No.: WO96/25496
PCT Pub. Date: Aug. 22, 1996

(30) Foreign Application Priority Data

Feb. 17, 1995 (EP) .................................................. 95200389

(51) Int. Cl.[7] .................................................. C12N 15/68
(52) U.S. Cl. .................. 435/69.1; 435/252.3; 435/320.1
(58) Field of Search .................................. 435/69.1, 69.7, 435/252.7, 720.1

(56) References Cited

PUBLICATIONS

Wu et al. Isolation of FSH from bovine pituitary glands. J. of Encodrin. 137:59–68, Jan. 1993.

Lindau–Shepard et al. "Identification of Amino Acids in the C–Terminal Region of Human Follicle–Stimulating Hormone (FSH) beta–subunit Involved in Binding to Human FSH Receptor". Endocrinology 135(3):1235–1240, Sep. 1994.*

Greenberg et al. "Expression of biologically active heterodimeric bovine follicle–stimulating hormone in milk of transgenic mice". P.N.A.S. 88:8327–8331, Oct. 1991.*

* cited by examiner

Primary Examiner—John Ulm
(74) Attorney, Agent, or Firm—Trask Britt

(57) ABSTRACT

The invention provides methods for the production of recombinant bovine Follicle Stimulating Hormone (bFSH) as well as vectors and cells for use in those methods. In particular the invention provides baculovirus based vectors which are capable of expression of bFSH in insect cells. bFSH is a heterodimeric protein belonging to a family of glycoprotein hormones which are produced in the pituitary or the placenta. It finds its use in many fertility related applications. Expression of bFSH in baculovirus/insect cell systems leads to a recombinant bFSH which has an unexpected high activity in a human FSH receptor assay and/or a bovine immature oocyte assay. The genes encoding the subunits of bFSH may be present on one baculovirus derived vector or on two or more vectors which are to be cotransfected.

17 Claims, 7 Drawing Sheets

PRODUCTION OF BIOLOGICALLY ACTIVE RECOMBINANT BOVINE FOLLICLE STIMULATION HORMONE (REC BFSH) IN THE BACULOVIRUS EXPRESSION SYSTEM

RELATED APPLICATIONS

This application claims priority from pending application PCL/NL96/0073 filed on Feb. 16, 1996 designating the United States of America, which itself claims priority from European Patent Application EP 95200389.5 filed on Feb. 17, 1995.

BACKGROUND

1. Field of the Invention

This invention relates to the field of recombinant expression in insect cells. It relates especially to the expression of heterodimeric proteins in such cells and more particularly to the expression of glycoprotein hormones such as follicle stimulating hormone and the like.

2. State of the Art

Follicle stimulating hormone (FSH) belongs to the family of glycoprotein hormones, which are produced either in the pituitary (LH, TSH) or in the placenta (hCG). Within a species, each of these hormones consists of a common α subunit, which is non-covalently bound to a hormone specific β subunit. Purified FSH administered alone or in combination with luteinizing hormone (LH), has been used to induce a superovulatory response. The results with these hormones or with pregnant mare serum gonadotropin (PMSG), which contains intrinsic FSH and LH activity, have been variable. The use of recombinant bovine FSH (rec.bFSH), which is guaranteed to be free of LH, and which is homologous to the species in which it is applied most frequently, may improve superovulation results. Furthermore, bovine FSH is difficult to purify in substantial quantities from bovine pituitaries (Wu et al., 1993). Rec.bFSH therefore may provide sufficient material to allow for structure-function studies by epitope mapping (Geysen et al., 1984; Westhoff et al., 1994).

cDNA's of bovine α subunit (Erwin et al., 1983; Nilson et al., 1983), as well as cDNA's of bovine FSH β subunit (Esch et al., 1986; Maurer & Beck, 1986) have been isolated.

As indicated in Table 1, recombinant FSH has been produced in chinese hamster ovary (CHO) cells for the human (Keene et al., 1989; Van Wezenbeek et al., 1990; Roth et al., 1993) and the ovine (Mountford et al., 1994) species, whereas for the bovine species recombinant FSH has been produced in CHO cells and in transgenic mice (Greenberg et al., 1991). Rec.bFSH has also been produced in mouse epithelioid cells (Chappel et al., 1988) and has been applied for superovulation in cattle (Looney et al., 1988; Wilson et al., 1989, 1993).

The baculo virus expression system is based on the infection of insect cells with a recombinant baculovirus (L. A. King and R. D. Possee, 1992) and is increasingly used for production of heterologous proteins. Insect cells have the glycosylation apparatus capable of synthesis of high mannose or hybrid type carbohydrates, as well as simple O-linked chains, and recombinant proteins can be expressed with much higher efficiency as compared with the chinese hamster ovary or COS cell system (Chen et al., 1991). The baculovirus expression system has been used to produce amongst others the α subunit of hCG (Nakhai et al., 1991a, b), the α subunit of carp gonadotropin (Huang et al., 1991; Chen and Bahl, 1991), the β subunit of hCG (Chen et al., 1991; Sridhar and Hasnain, 1993; Sridhar et al., 1993; Nakhai et al., 1992; Jha et al., 1992), hCG (Chen and Bahl, 1991; Nakhai et al., 1992), the receptor for human FSH (Christophe et al., 1993) and, quite recently, human FSH (Lindau-Shepard et al., 1994; Dias et al., 1994) (Table 1). Co-expression of two, or more, proteins by the baculovirus expression system has been achieved for instance by construction of a multiple expression transfer vector containing two, or more, foreign genes each of which is under the control of a copy of the p10 or polyhedrin promoter. Such expression vectors have been applied to the production of 2 totally unrelated proteins, for instance luciferase and hCG β (Hasnain et al., 1994), but also to the production of 3 or 4 closely related proteins, which may be assembled in vivo to complex structures (Belayev and Roy, 1993). Such a system might also be used for co-expression of FSH α and FSH β, including the bovine forms. However, the synthesis of protein complexes has also been accomplished by co-infection of insect cells with two different recombinant viruses. This has been applied to bluetongue virus proteins (French, Marshall & Roy, 1990), hCG (Chen & Bahl, 1991) and hFSH (Lindau-Shepard et al., 1994). Here we report for the first time the synthesis of bovine FSH in insect cells, by co-infection of cells with two recombinant viruses carrying the genes of bFSHα and bFSHβ, respectively. This bFSH appears to be active in at least three different bioassay systems. Production in insect cells of only bFSHα was about 10 times higher than of only bFSHβ, but co-infection of the two recombinant viruses resulted in production of heterodimer at a level comparable to that of bFSHα alone. A similar effect has been observed with the production of recombinant ovine FSH in Chinese hamster ovary cells (Mountford et al., 1994), and of recombinant hCG in monkey cells (Reddy et al., 1985).

TABLE 2

Production level[1] (IU/ml for bioassays, and μg/ml for ACA and specific activity[2] (IU/μg) of rbFSH

| assay | batch 1/7/94 |
|---|---|
| $Y_1$ morphol[3] | 8.54 8.54 8.54 4.27 |
| x ± S.D. | 7.47 ± 2.14 |
| S.A. | 2.49 |
| $Y_1$ cAMP[4] | 19.1 29.9 23.9 |
| x ± S.D | 24.3 ± 5.41 |
| S.A | 8.1 |
| Sertoli cell[4] | 13.7 4.4 2.7 |
| x ± S.D. | 6.90 ± 4.83 |
| S.A. | 2.3 |
| OMI | 15.0 31.0 |
| x ± S.D. | 23.0 ± 11.3 |
| S.A. | 7.7 |
| ACA | 1.8 1.6 5.6 |
| x ± S.D. | 3.0 ± 1.8 |

[1] harvest at 72 hours after infection (p.i.), except when indicated

[2] $S.A. \frac{IU/ml \text{ (biossay)}}{\mu g/ml \text{ (ACA)}}$

[3] measurement of change in cell morphology

[4] measurement of cAMP (½ max. level), except when indicated.

Up to now no reports have been presented describing baculo expression of bovine FSH.

A surprising effect, obtainable by expressing bovine FSH in baculovirus based systems, is that very high biological activity is found, as demonstrated both in a heterologous system containing human FSH receptors, and in a homologous system containing bovine immature oocytes. It appears that the biological activity of baculo-derived rbFSH is at least as high as native FSH purified from pituitaries, or as rbFSH produced in higher eukaryotic cell systems.

This leads directly to an application in humans, especially in those cases in which administration of FSH needs to be carried out only a limited number of times, or in which the application can be carried out in vitro. Furthermore parts of the rbFSH molecule may act as an FSH antagonist and therefore can be used as a male contraceptive. This will only be possible if (fragments of) bovine FSH produced in baculovirus systems will not be immunogenic, and can therefore be used in humans without restrictions. Alternatively, bFSH or fragments of it may be used for vaccination against FSH as a means of contraception in the male. In the human this could be an attractive alternative for the use of hFSH, because a heterologous hormone (or part of it) may be more immunogenic than the homologous hormone.

For the bovine species the results of the oocyte maturation inhibition test lead to application in superovulation treatments in the bovine, where it can act as a substitute for Pregnant Mare Serum Gonadotropin (PMSG) or other hormones with FSH activity, in the treatment of reproductive problems such as anoestrus incomplete follicle development etc. It can also be used in in vitro experiments, for instance for the purpose of in vitro maturation and fertilization of oocytes. The biological activity of baculo-derived rbFSH in a rat-Sertoli-cell assay and a $Y_1$ cell assay indicates that this biological activity most likely is not species specific. Applications therefore can be expected in other species than the human, bovine or rat, both in vivo and in vitro.

The invention further allows one to tailor the degree of sialylation, and thus the metabolic clearance rate and in vivo biological activity of FSH, by cloning the transsialydase-gene into the subunit-gene(s) containing baculo-vector. This may allow for addition of neuraminic acid to the glycan cores of rbFSH, and thus for increased biopotency.

Another part of the invention provides for fusion of (parts of) the bFSHβ- and bLSHβ-gene in order to tailor chimaeric hormones with a fixed ratio of FSH to LH bioactivity.

It will be understood that these kind of applications and embodiments lie within the scope of the present invention. Thus, where FSH is used in the present application this must be read as including fragments and/or derivatives thereof. It will also be clear that the exemplified vectors and/or regulatory elements are only examples and that other vectors capable of expression in insect cells will be suitable as well, as will other regulatory elements. The cloning techniques are also known in themselves and may be varied. The exemplified cell line is a well known and often used insect cell line. Other cell lines capable of being transfected by the vectors of the invention will also be applicable. Culture media for the transfected cells can be suitably selected by the person skilled in the art. Once bovine FSH has been expressed it is known how to isolate it from the culture. Once isolated and/or purified pharmaceutical preparations can easily be formulated using the knowledge obtained with other recombinant or isolated gonadotropins.

The invention will be explained in more detail in the following experimental part.

Figure 1A:
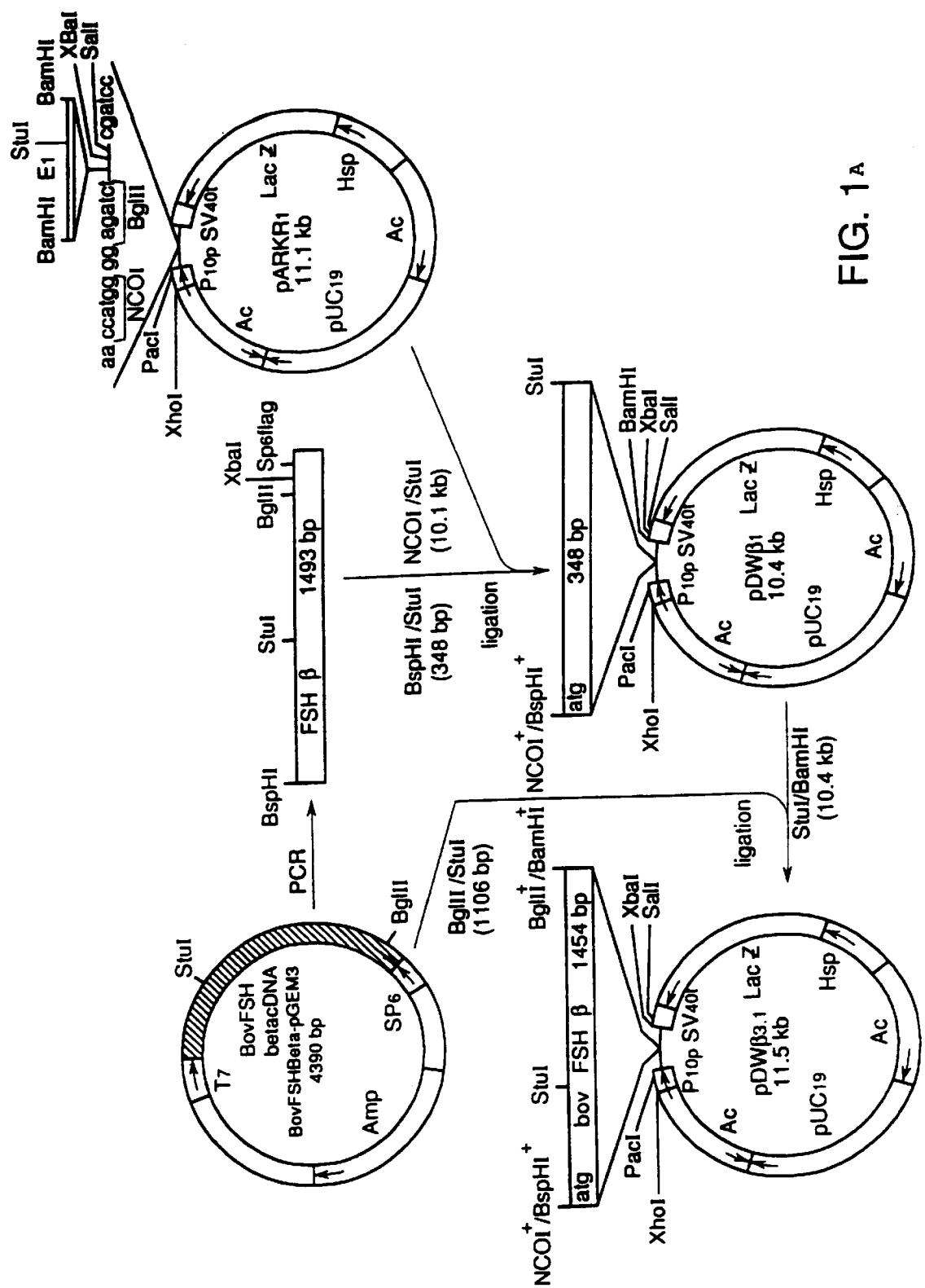
FIG. 1A and FIG. 1B

Scheme of the construction of transfer vectors pDWα9.1 and pDWβ3.1. Arrows show the directions of transcription of the hsp70 (Lac Z), T7, Sp6 and 10 promoters. Ac, ACNPV DNA; p10, p10 promoter, hsp70, Drosophila melanogaster hsp promoter; $SV_{40t}$, $SV_{40}$ transcription termination sequence, Lac Z, *E. coli* lac Z gene; B, BamH I; E, EcoR I; H, Hind III; X, Xho I, PCR, polymerase chain reaction; Pa Pst I; N, Nco I; stop, stopcodons, S, Sal I; Bg, Bgl II; Sm, Sma I; Sa, Sac I; $E_1$, Hog cholera virus glycoprotein El, Amp, ampicillin resistance gene.

FIG. 2

Radio immuno precipitation assay with polyclonal bFSHα antiserum (Parlow #5551791), polyclonal bFSHβ antiserum (Parlow #899691), monoclonal antibody against hFSHβ (code ME.112, MBS, Maine, USA) and monoclonal antibody against hFSHα (code ME.111, MBS, Maine, USA).

Culture media and cell lysates of Sf21 cells were analyzed after infection with AcNPV/$α_{3.4}$, AcNPV/$β_{1.4}$ or AcNPV/$MO_{21}$ (control). Cells were labeled at 42 h after infection with 40 μCi of [$^{35}$S]methionine per ml for 6 h. Immunoprecipitates were analyzed by SDS-12% PAGE and visualized by autoradiography. A. bFSHα. B. bFSHβ.

Lanes: 1 and 6, mol. weight markers (rainbow trout), M.W.×10$^3$; 2 and 7, AcNPV/$MO_{21}$ (wt) cell lysate; 3 and 8, recombinant AcNPV/($α_{3.4}$ or $β_{1.4}$) cell lysate; 4 and 9, recombinant AcNPV/($α_{3.4}$ or $β_{1.4}$) medium; 5 and 10, AcNPV/$MO_{21}$ (wt) medium.

Polyclonal antisera were used in lanes 2–5, and monoclonal antibodies were used in lanes 7–10.

FIG. 3

Time course of production in Sf21 cells infected with AcNPV/$α_{3.4}$ (o–o) or AcNPV/$β_{1.4}$ (Δ–Δ) alone, or with AcNPV/$α_{3.4}$ plus AcNPV/$β_{1.4}$ (°–°).

ELISA concentrations of bFSHα and bFSHβ, and ACA (antigen capture assay) concentrations of bFSHαβ in culture media at 18, 24, 41, 48, 65, 72, 92, 96 and 150 h after infection are shown. Concentrations are expressed in μg (per 10$^6$ cells) of reference preparations bLHα-AFP-3111A, USDA-bFSH-beta and bFSH-io58.

FIG. 4

Effect of rbFSH or subunits on GVBD in bovine cumulus-enclosed oocytes in vitro.
ON=oocyte nucleus stage (GV stage)
M=metaphase
D=diakynese
LD=late diakynese
T=telophase
C=negative control
+C=positive control (bFSH 0.25 IU.ml$^{-1}$)
α=rbFSHα
β=rbFSHβ
α+β=rbFSHαβ

Numbers on top of the bars indicate numbers of oocytes tested.

FIG. 5

Analysis of immunoactivity and bioactivity in a $Y_1$ cell assay of affinity purified rbFSH.

FIG. 6

Analysis of immunoactivity and bioactivity in a Sertoli cell assay of affinity purified rbFSH.

DETAILED DESCRIPTION OF THE INVENTION

Experiments
Materials and methods
Viruses and cells

Autographa californica Nuclear Polyhedrosis Virus (AcNPV) and recombinant virus stocks were propagated in Spodoptera frugiperda clone-21 (Sf21) cells grown as monolayers in TC100 medium (GIBCO—BRL), supplemented with 10% fetal calf serum plus antibiotics. For cotransfection, Sf21 cells were grown in Grace medium (Grace, 1962), supplemented with 10% foetal calf serum plus antibiotics. For immunological assays like RIP or IPMA and for protein production, Sf21 cells were grown in Sf900 serum-free medium (GIBCO—BRL) plus antibiotics. In order to reduce the background of wild type virus, modified AcNPV in which the p10 gene was exchanged for a synthetic and unique BSU36I restriction site was used for cotransfection (Martens et al.,1994). After homologous recombination between wild type virus and the transfer vector, circular recombinant viral DNA will be formed, which can infect Sf21 cells. Non-circular DNA is not infectious, and therefore background will be reduced. However, due to non-homologous recombination, background percentage will be reduced from 95% to 70% only (Martens, 1994).

Enzymes and chemicals

Restriction enzymes and phage T4 DNA ligase were purchased from Biolabs (USA) and used as recommended by the supplier. $^{35}S$ methionine was obtained from Amersham UK. VenR ™DNA polymerase was from Biolabs (USA). All cloning procedures were carried out essentially according to Sambrook et al. (1989).

Plasmids, and construction of transfer vectors

Figure 1B:
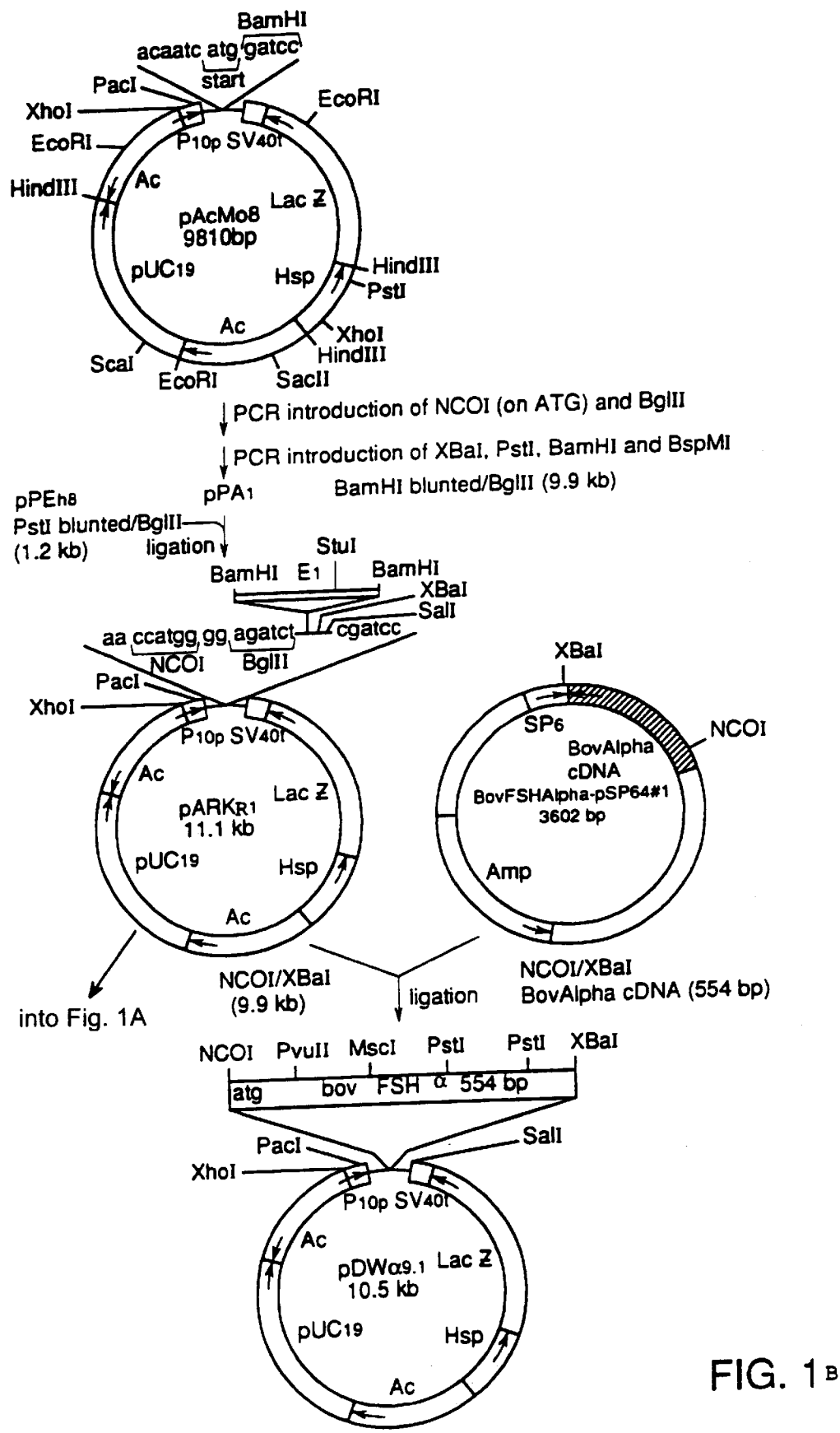

The cDNA coding for bFSHα was purified after double digestion of the plasmid bov Alpha-pSP64 #1 (Leung et al., 1987) with Nco I plus XBa I. The DNA of 554 bp's contained a signal sequence of 72 bp at the 5' end, and an untranslated region of 188 bp at the 3' end. It was cloned into the unique Nco I and XBa I sites of vector pARKhl which is a derivative of transfer vector pAcAs3 (Vlak et al., 1990). The Nco I site contained an ATG codon which coincided exactly with the start of the signal sequence of bFSHα. Correct insertion with respect to the p10 gene of bFSHα in the vector was confirmed by extensive restriction enzyme analysis and sequencing (dideoxy method), and the selected transfer vector was designated pDWa9.1 (See FIG.1A and FIG. 1B).

DNA coding for bFSHβ was obtained by amplification of the relevant region of Bov FSHbeta pGEM3 (Maurer and Beck, 1986) by the polymerase chain reaction (PCR). A 39-cycle amplification was performed with Ven DNA polymerase. The sequences of the synthetic oligonucleotides used in PCR reactions were as follows
(5' 3'): 1, C C T G A G A G A T C T A T C A T G A A G T C T G T C C A G T T C T G (SEQ. ID. NO. 1); 2, G A G G G A T C C A G A T C T A G A G G A T T T A G G T G A C A C T A T A (SEQ. ID. NO. 2).

Primer 1 introduced a BspH I restriction site by changing the sequence A G G A T G A A G into A T C A T G A A G, which allowed cloning of the bFSHβ-cDNA on the ATG at the start of the signal sequence. Primer 2 introduced a combined Bgl II/XBa I restriction site and a SP6 flag at the 3' end of bFSHβ-cDNA.

After PCR, the bFSHβ-cDNA of 1.5 kb length was purified by electrophoresis in a 4% agarose gel, and doubly digested with BspH I/Stu I. A 348 bp DNA fragment was isolated and cloned into the unique Nco I and Stu I sites of the vector pARKhl. The recombinant plasmid was termed pDWβ$_1$.

Vector pARKh$_1$ was derived from vector pAcAs$_3$ (Vlak et al., 1990). pAcAs$_3$ is a transfer vector of 9809 bp, containing the baculovirus p10 promoter, directly flanked by a unique BamH I site. The nucleotide sequence around this BamH I site was first modified by PRC in such a way, that an ATG start codon was formed; the resulting plasmid was called pAcMo8 (Vlak & van Oers, 1994). Further modifications by PCR introduced a multiple cloning site (MCS) containing a Nco I site, followed by Bgl II, Xba I, Pst I and BamH I. This plasmid was called pPA$_f$. A synthetic MCS plus hybrid envelope glycoprotein of hog cholera virus ($E_1$) plus 3 stop codons were inserted by cloning Bgl II+blunted PSt I of pPEh8 (van Rijn et al., 1992) into Bql II+blunted BamH I of pPA$_1$, resulting in transfer vector pARKh$_1$. Hybrid $E_1$ contains a unique Stu I site, which allowed for the exchange of $E_1$ for bFSHβ. bFSHβ was cloned into pARKh$_1$ in two parts. The 5' part was obtained by PCR, and the 3' part by regular DNA isolation from miniprep plasmid DNA (348 bp DNA fragment; see above) of Bov FSHβ pGEM$_3$. This strategy was chosen in order to minimize possible errors, which can be introduced by amplification via PCR.

Plasmid BovFSHβ pGEM$_3$ was digested with Stu I and Bgl II. Because of methylation of the Stu I restriction site, this site was only partially digested. A 1106 bp fragment was isolated by excision from a 4% agarose gel and purified according to standard techniques. This fragment was ligated into the Stu I/BamH I sites of vector pDWβ1. Before transformation, the ligation mixture was digested with Bgl II for the purpose of background reduction. The resulting recombinant plasmid pDWβ3.1 now contains a 1454 bp bFSHβ fragment consisting of a 57 bp 5' fragment encoding the signal sequence, a 330 bp fragment coding for bFSHβ, and a 1067 bp 3' untranslated region, and it had an ATG codon exactly at the start of the signal sequence (See FIG. 1A and FIG. 1B).

The correct orientation of the bFSHβ gene with respect to the p10 promoter was confirmed by extensive restriction enzyme analysis and by sequencing the ligation regions.

Construction of baculovirus recombinants expressing bFSHα or bFSHβ

Viral AcNPV DNA isolated from extracellular budded virus particles (0.15 μg) was completely digested with BSU36I (30 U/μg/h, for 5 hours). DNA was purified by standard procedures and dissolved in 15 μl 1 mM Tris/0.1 mM EDTA buffer (pH 8.0; TE buffer).

Confluent monolayers of Sf21 cells (7.5 to 8×10$^6$) grown in 9 cm diameter petri dishes were cotransfected with 0.1 μg of digested viral AcNPV DNA, and 2 to 3 μg of transfer vector DNA by the calcium phosphate precipitation technique described by Summers and Smith (1987).

After transfection, cells were washed with TC-100 medium, and covered with 16 ml of a TC100 agar overlay, containing 60 μg Bluo—Gal (GIBCO—BRL) per ml. Cells were grown for 4 to 6 days, and blue plaques were picked and were further plaque purified in M6 plates (Costar). Plaque purification was repeated until no more white plaques of wild type virus could be observed. Purified blue plaques were used to infect confluent monolayers of Sf21 cells in M24 plates (Costar). After 4 days, the cells were fixed and tested for expression of bFSH subunit by an immune peroxidase monolayer assay (Wensvoort et al., 1986), after incubation with a 1:1000 dilution of polyclonal rabbit antiserum against either bFSH (a gift from J. Closset and G. Hennen) or oFSH (H. Westhoff), or bFSHβ (USDA-5-pool, a gift from D. Bolt). Media were tested for presence of bFSH subunit by ELISA in M96 microtiter plates (Costar); 10 μl of medium was coated (0.05 M carbonate buffer, pH 9.65/1 hr/37° C.) onto the bottom of a well and incubated with rabbit polyclonal antisera against either bFSHα or bFSHβ (A. F. Parlow). Plaque-purified viruses both for bFSHα and bFSHβ were selected, and were used for preparation of virusstocks. After double infection with a recombinant virus containing bFSHα plus a recombinant virus containing bFSHβ, media were analyzed for bFSH heterodimer in an antigen capture assay (ACA) based on trapping of bFSHαβ in a 96 wells plate, coated with a commercial monoclonal antibody (MCA, code ME.112) against human FSHβ (MBS, Maine, USA) This MCA was shown to crossreact with bFSHβ. The wells were then incubated with rabbit anti-bFSHα polyclonal antisera (A. F. Parlow) followed by HRPO-conjugated rabbit-anti-guinea-pig-IgG (RAGPPO, Dako, Denmark) and substrate solution (with tetra mehyl benzidine as the chromogen). Reference preparations bFSHα, bLHα, bFSHβ, bFSHαβ were a gift from D. Bolt and A. F. Parlow, and bFSHαβ, bFSHα and bLHα were a gift from J. Closset and G. Hennen (Univ. of Liège, Belgium).

DNA analysis

Viral and cellular DNAs were isolated from Sf21 cells infected with wild type and recombinant AcNPV viruses as described by Summers and Smith (1987). Restriction enzyme-digested viral and cellular DNAs were analyzed by electrophoresis on a 4% agarose gel, and it was shown that the DNA sequences encoding bFSHα and bFSHβ were correctly inserted in the p10 locus of baculovirus.

The nucleotide sequence of the junctions between bFSH subunit and transfer-vector DNA were determined by the dideoxy chain termination method with $T_7$ DNA polymerase (Pharmacia) and primers (5' 3') pAcAs—upi (CAACCCAACACAATATATT) (SEQ. ID. NO. 3) and pAcAs—rupi (GGTTACAAATAAAGCAATAGC) (SEQ. ID. NO. 4).

Radiolabelina and analysis of proteins

Radiolabeling and analysis of recombinant proteins with $35_S$ methionine (Amersham, UK) were done as described by Hulst et al. (1993). For immunoprecipitation of bFSHβ, either monoclonal antibody against human FSHβ (ME.112, commercially obtained from MBS, Maine, USA) or polyclonal guinea pig anti-bFSHβ antiserum (A. F. Parlow) were used, whereas for bFSHα polyclonal guinea pig anti-bFSHα (A. F. Parlow) was used. (Monoclonal ME.111 against hFSHα was also used, but did not cross-react with bFSHα.)

ELISA and antigen capture assay (ACA)

bFSHα and bFSHβ subunits, expressed by recombinant viruses, were detected by specific ELISA systems. M96 plates (Costar) were coated with medium (maximally 10 μl /well) collected from Sf21 cells which were infected with either AcNPVα3.4 or AcNPVβ1.4. Coated wells were then incubated (1 h/37° C.) with 1:1000 diluted polyclonal guinea pig anti-bFSHα or -bFSHβ antisera (A. F. Parlow). Bound immunoglobulins were detected with 1:500 diluted rabbit-anti-guinea-pig-IgG coupled to horseradisch peroxidase (RAGPPO, Dako, Denmark), and tetramehylbenzidine as substrate. Optical density was measured at 450 nm. Purified pituitary bFSHα (Closset and Hennen) and bFSHβ (USDA-bFSH-beta; Bolt) were used as reference preparations (1, 10, 20, 40, 80 ng/well) for quantitative measurement. Bovine FSHαβ heterodimer expressed after double infection (at MOI>10) with recombinant viruses AcNPVα3.4 plus AcNPVβ1.4 was detected by antigen capture assay (ACA) as described by Wensvoort et al. (1988).

Briefly, monoclonal antibody against human FSHβ (a commercial preparation of MBS, Maine, USA, crossreacting with bFSHβ and bFSHαβ) was used as capture antibody in a dilution of 1:100 (1 μg/100 μl/well) by coating it on a M96 well (1 h/37° C.). Medium (maximally 100 μl/well) harvested from doubly infected Sf21 cells was incubated in coated wells (1 h/37° C.) and bound bFSHαβ was detected by sequentially incubating with 1:1000 diluted polyclonal guinea pig anti bFSHα (A. F. Parlow) (1 h/37° C.) and RAGPPO (1 h/37° C.).

The substrate reaction was as described for the ELISA. Purified pituitary bFSHαβ (USDA-bFSH-I-2, D. Bolt, or bFSH from J. Closset and G. Hennen) was used as reference preparation (1–80 ng/well) for quantitative measurements. (It should be noted that measurement of bFSHαβ in this system may lead to underestimation because of blocking of capture antibody by free bFSHβ subunits.)

Time course of production of subunits or heterodimer

The time courses of production of rec.bFSHα, rec.bFSHβ and rec.bFSHαβ were determined essentially as described by Hulst et al. (1993). Media were clarified by centrifugation for 10 minutes at 1000×g, and were analysed by ELISA (subunits) or ACA (heterodimer).

$Y_1$-cell bioassay $Y_1$ mouse adrenal cells, stably transfected with cDNA for the human FSH receptor (coupled to the gene for resistance to methotrexate) were kindly donated by ARES, Serono, Rome, Italy. Those cells respond to FSH stimulation with cAMP accumulation, progesterone synthesis and a change in cell morphology. Unstimulated cells grow flat on the surface, but after addition of a cAMP stimulating agent the cells round off. This change in cell-morphology is maximal after two to three hours and disappears after approximately 7 hours. The optical density (O.D.) of the cells changes after rounding off and can be measured with an ELISA reader, at 405 nm. The rounding off shows good correlation with cAMP accumulation (Westhoff et al., 1994). Cells were plated in M96 plates in Ham's F10 medium (GIBCO) supplemented with 2 mM 1-glutamine. The incubation with FSH was carried out in Ham's F10 medium, and O.D. was measured after 0.5, 1, 2, 3, 4, and 6 h incubation. At 2 and 4 hours the rounding off was also determined light-microscopically by the naked eye. One hundred μl aliquots of media were harvested at 2 hrs, for cAMP determination (cAMP $^3$H assay systems, Amersham TRK 432, UK). The minimal dose of bovine FSH (USDA-bFSH-I-2) giving a significant response in the $Y_1$ cell assay is 4 ng/ml, ovine FSH (oFSH, NIADDK—oFSH-16, AFP-5592C) 30 ng/ml, and of porcine FSH (pFSH, NIH—FSH—P-1) 200 ng/ml.

Rat Sertoli-cell bioassay

The rat Sertoli-cell bioassay was done as described by Oonk et al. (1985) and Oonk & Grootegoed (1987). Culture media were harvested, and analyzed for cAMP concentrations (cAMP $^3$H assay systems, Amersham TRK 432, UK)

Oocyte-maturation inhibition bioassay

In vitro maturation of isolated oocyte-cumulus complexes can be inhibited by a amanitin containing culture media in combination with small doses of FSH. Bovine oocyte-cumulus complexes were isolated from fresh slaughterhouse material, and tested for maturation inhibition (i.e., absence of germinal vesicle break down, GVBD) by FSH according to Hunter and Moor (1991).

Affinity chromatography and analysis of immunoactivity of rbFSH

Recombinant bFSH was purified by affinity chromatography, using a monoclonal antibody—against human FSHβ subunit—coupled to CNBr activated Sepharose (Sepharose 4B, Pharmacia). 1.5 Gram of Sepharose 4B was washed and allowed to swell as recommended by the manufacturer. Monoclonal antibody (Mab) against human FSHβ (code ME.112, Maine Biotechnology Services, Inc., Portland, Me., USA), 9 ml containing 9 mg of purified lgGl, was dialysed overnight against 1 L of couplingbuffer (0.1 M NaHCO$_3$/0.5 M NaCl pH 8.3). The resulting Mab solution (8 ml) was incubated with 5 ml of swollen gel (overnight, 4° C., end-over-end mixing). Coupling efficiency by A280 measurement was 98%.

After washing with coupling buffer, 0.1 M Tris pH 8.0, 0.1 M acetate/0.5 M NaCl pH 4 and 0.1 M Tris/0.5 M NaCl pH 8 respectively, the coupled Mab was incubated with 130 ml sterile (0.2μ filter) Sf900 insect cell culture medium (Gibco) containing rec. bovine FSH αβ heterodimer (approximately 1 μg/ml by immunoassay).

As a control experiment, 2 ml of coupled Mab was mixed with 30 ml sterile (0.2μ filter) Sf900 insect cell culture medium containing rec. bovine FSHα had been harvested at 72 hours after infection. Binding reactions were allowed to proceed for 24 hours at 4° C., under gentle shaking.

The sediment was separated by centrifugation (10'/500 g/4° C.) and supernatants were kept apart for determination of binding efficiency. Columns were packed in pasteur pipets with bed volumes of approx. 2 ml and 1.5 ml for rb FSHαβ was eluted stepwise with sterile cold (ice) PBS (10 ml), and 0.1 M glycine HCl/0.1 M NaCl buffer with pH 4.0 (6 ml), pH 3.5 (6 ml), pH 3.0 (7 ml), pH 2.5 (6 ml) and pH 2.0 (5 ml) respectively. 1 ml fractions were collected on ice, and pH was immediately neutralised with 3 M Tris. All fractions were stored at −20° C. until assayed.

Analysis of immunoactivity was performed by antigen capturing assay (ACA) whereas bioactivity was determined by two in vitro bioassays, i.e. $Y_1$ cell assay and Sertoli cell assay. Furthermore, fractions were concentrated (10X) on 'Centricon 10 or Centricon 30 filters (Amicon, Inc. Beverly, Mass., USA) and analysed for purity and protein content by SDS—Page (12%) under non-reducing conditions and staining with silver.

Results

Construction, selection and characterization of recombinant viruses expressing bFSHα or bFSHβ

Transfer vectors pDWα9.1 and pDWβ3.1 were constructed as depicted in FIG. 1.

S f21 cells were cotransfected with pDWα9.1 or pDWβ3.1 and wild-type (wt) AcNPV/$MO_{21}$ DNA isolated from extracellular virus particles. In this wt virus, the p10 coding sequence is replaced by a BamH I oligonucleotide linker with a unique BSU36I recognition site (Martens et al., 1994). This allows for an increased proportion of recombinants after eliminating the parental virus by linearization.

Polyhedrin-positive plaques expressing β-galactosidase were isolated and analyzed for expression of bFSHα or bFSHβ by immunostaining of cells with polyclonal rabbit antisera, and by ELISA of culture media with polyclonal guinea pig antisera (A. F. Parlow). One plaque-purified bFSHα virus (AcNPV/α3.4) and one plaque-purified bFSHβ virus (AcNPV/β1.4) were used to prepare virusstocks with a tissue culture dose of infection (TCID) of approximately 7 and 8, respectively.

Figure 2:
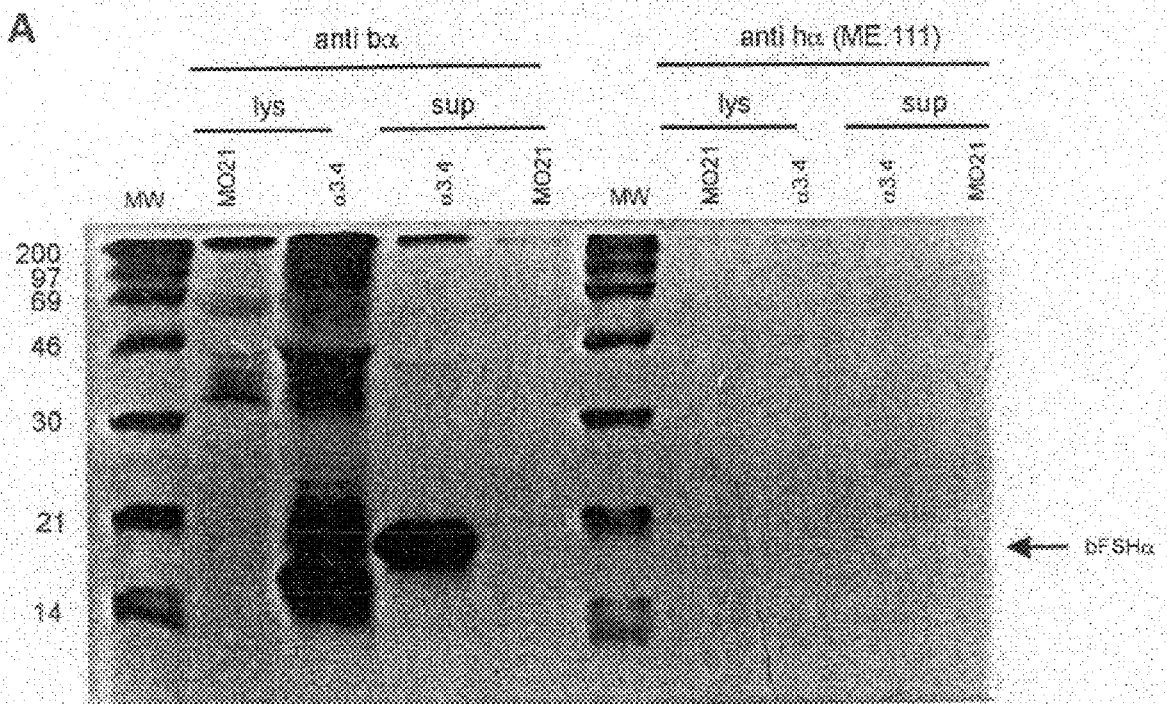
Figure 2:
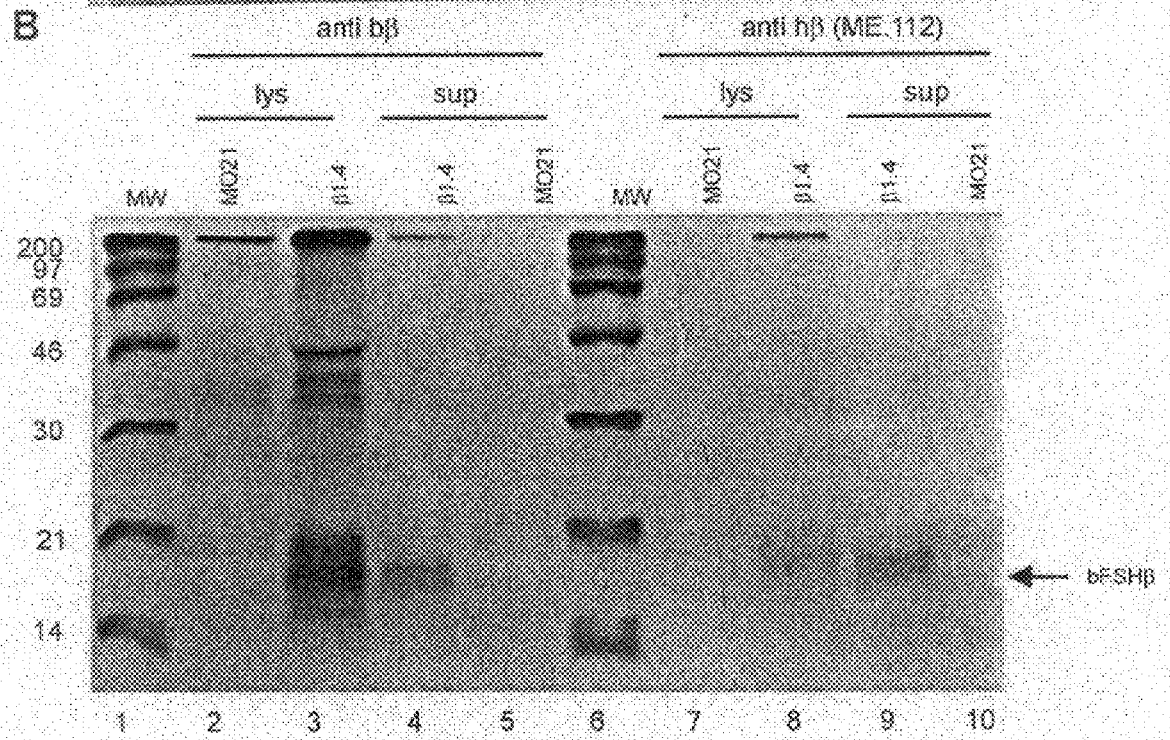

The α and β expression products were further characterized by radio immuno precipitation (FIG. 2a+b). bFSHα, which was precipitated from the medium of Sf21 cells infected with AcNPVα3.4, migrated as a single band with a molecular mass of approx. 18 kD (FIG. 2a, lane 4). Cell lysates showed a variety of labeled bands, which may be due to the use of polyclonal instead of monoclonal antibodies (lane 3). Monoclonal antibody against hFSHa (MBS, Maine, USA) did not precipitate any bFSHα, which was expected as this antibody did not show cross reaction with bovine a subunit in the ELISA.

bFSHβ, which was precipitated from the medium of Sf21 cells infected with AcNPV/β1.4, migrated as a doublet, with a molecular mass of 15–16 kD, both with polyclonal antisera (FIG. 2b, lane 4)(guinea pig anti-bFSHβ, A. F. Parlow) and monoclonal antibody (anti hFSHβ, MCS, Maine, USA) (lane 9). In cell lysates a doublet of slightly higher molecular weight was observed with both antibodies (lanes 3 and 8).

Expression and secretion of bFSHα and bFSHβ

Figure 3:
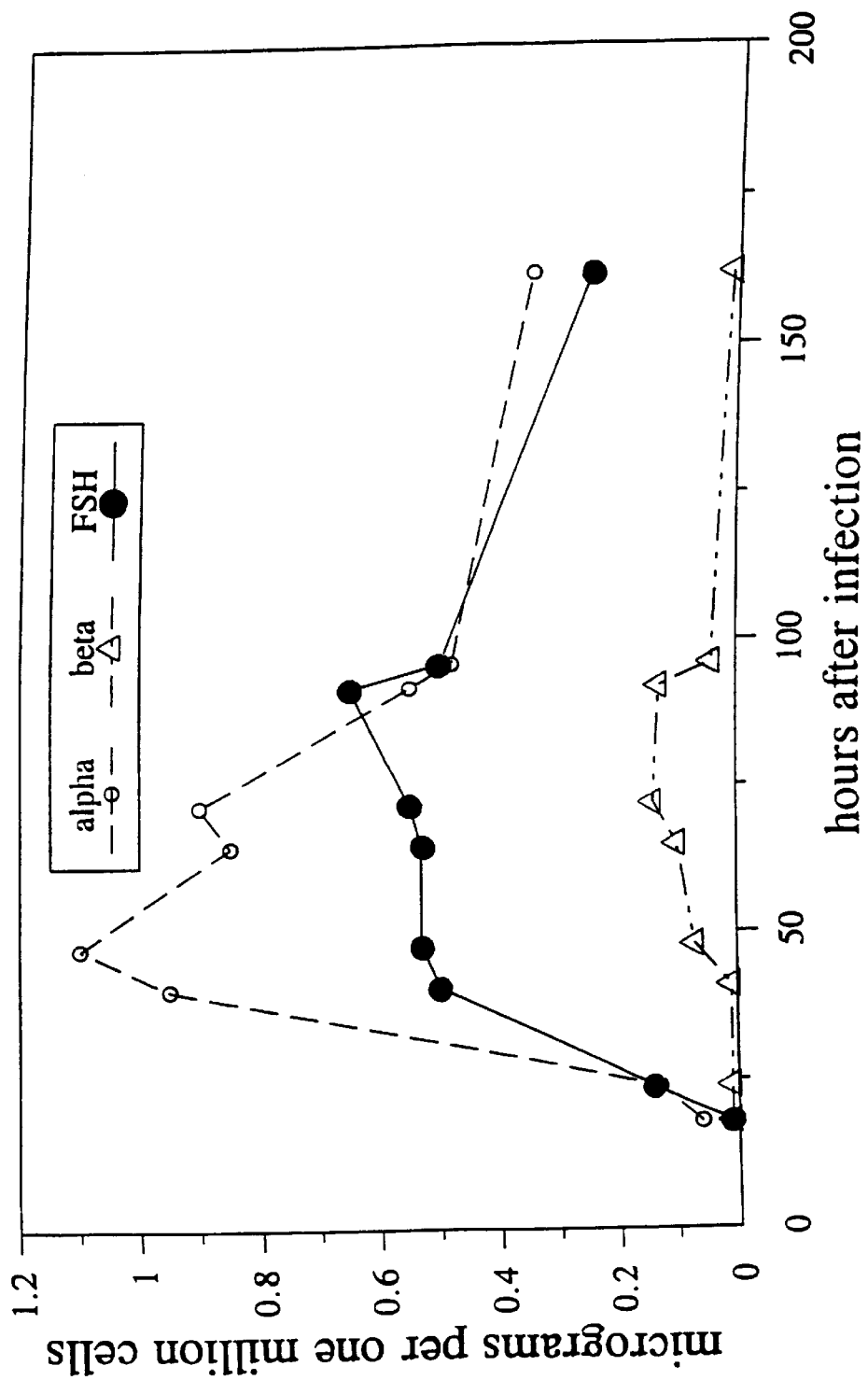

The levels of expression of bFSHα, bFSHβ and bFSHαβ in the medium of infected Sf21 cells were determined at different time intervals after infection, and the levels in Sf21 cell lysates were determined at 162 hours after infection, by specific ELISA systems and ACA (FIG. 3). The majority of bFSHα, bFSHβ and bFSHαβ was secreted into the medium, and only very small amounts were found in the cell lysates. Levels of bFSHα in medium were approximately 10 times higher than levels of bFSHβ, whereas levels of bFSHαβ were intermediate. Reference preparations used were bLHα:AFP0.3IIIA (Parlow), bFSHβ: USDA-bFSH-beta-subunit (Bolt) and bFSHαβ: UCB-i028 (Hennen/Closset). The maximum concentration of bFSHα was 1.1 μg/$10^6$cells/ 0.5 ml at 48 hours after infection (p.i.). For bFSHβ the maximum was 0.13 μg/$10^6$cells/ 0.5 ml at 72 hours p.i., and for bFSHαβ the maximum was 0.65 μg/$10^6$cells/0.5 ml at 92 hour p.i. In cell-lysates, bFSHα- and bFSHβ- concentrations were below the detection limit of the assay, and bFSHαβ-concentration was less than 0.01 μg/$10^6$cells.

$Y_1$-cell bioassay

In vitro bioassays were done on 5 ml aliquots of media (TC100) containing bFSHα and bFSHβ; these media were first concentrated (20×) by speedvac, and then mixed and incubated (16 h/27° C.) according to Nakhai et al. (1992).

Concentrated media containing bFSHα, bFSHβ or bFSH (α+β) were serially diluted and added to $Y_1$ cells. It appeared that no change in morphology could be observed with either bFSHα or bFSHβ, but distinct responses could be observed with bFSHαβ up to a 1:20 dilution of concentrated media.

In another experiment, $Y_1$-cell in vitro bioassays were done on SF900 media (serumfree) of Sf21 cells infected with either AcNPVα3.4 or AcNPVβ1.4 alone, or with AcNPVα3.4 plus AcNPVβ1.4. These media were directly diluted, without prior concentration by speedvac.

It appeared that media containing only bFSHα or bFSHβ did not induce a change in cell morphology, but media from cells infected with AcNPVα3.4 plus AcNPVβ1.4 showed very clearly FSH-specific responses up to a dilution of 1:800, which corresponds to a biological activity of 8–15 IU.ml$^{-1}$ (ref.prep. USDA-bFSH-I-2; 854 IU.mg$^{-1}$). This indicates that the yield of bFSHαβ after double infection was approximately 800 times higher than after reassociation of separately produced bFSH subunits; however, there may have been also a non-specific inhibitory effect of concentrated TC100 medium on $Y_1$ cells.

Media harvested from $Y_1$-cell cultures were analyzed for cAMP. It appeared that $Y_1$-cells which were incubated with baculomedia from doubly infected Sf21 cells showed dose-dependent cAMP responses.

Comparison with a (freshly prepared) reference preparation of bFSH (USDA-bFSH-I-2), gave a bioactivity of 20–024 IU/ml, whereas bioactivity of both single subunit-containing media was zero.

Rat-Sertoli-cell assay

Bioactivity of rbFSH media as determined in a rat-Sertoli-cell in vitro bioassay by comparison with USDA-bFSH-I-2 as a reference preparation, varied between 4 and 9 IU.ml$^{-1}$; again single subunit-containing media were negative. Maximal stimulation however of rbFSH was lower by a factor 2 to 4 as compared to USDA-bFSH-I-2. This may be due to differences in glycosylation between pituitary and recombinant bFSH.

Figure 4:
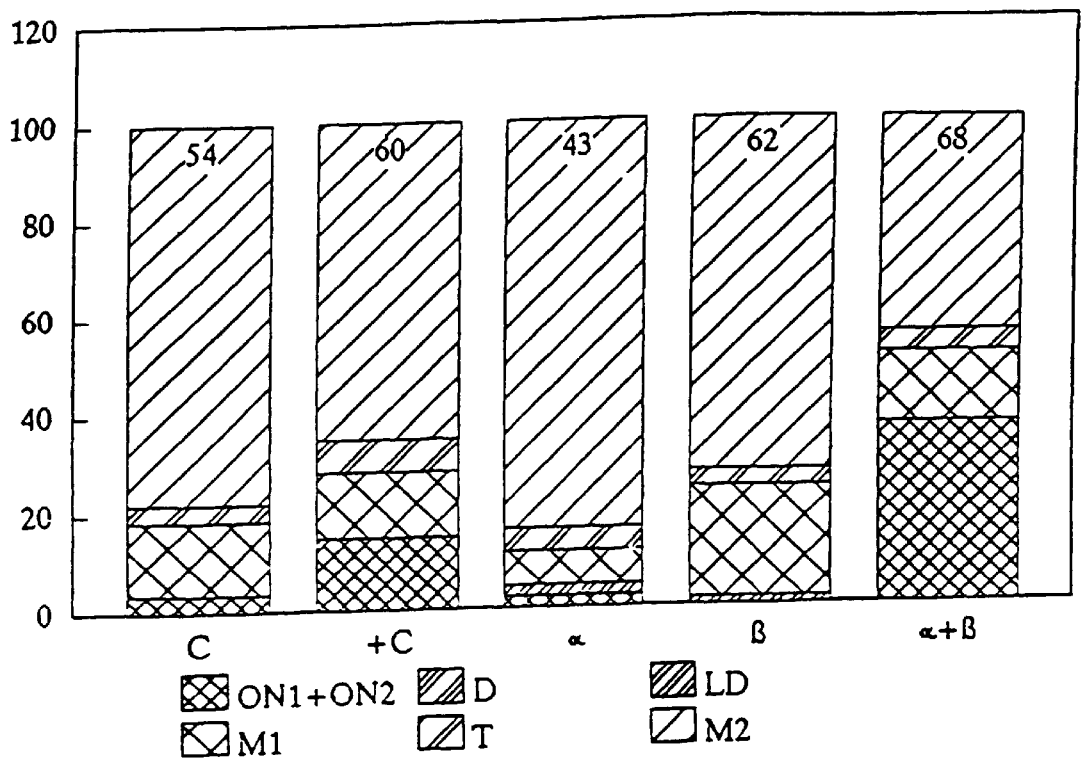

Oocyte-maturation inhibition assay rbFSH culture media was tested at a dilution of 1:25 in a bovine oocyte-cumulus in vitro bioassay, with bovine FSH from Sigma (25 $S_1$ U/vial) as a reference preparation. A bioactivity for rbFSH was found of 6.3 IU.ml$^{-1}$, whereas for rbFSHα- and rbFSHβ-subunits no bioactivity was observed (FIG. 4).

Affinity chromatography and analysis of immunoactivity of rbFSH

Figure 5:
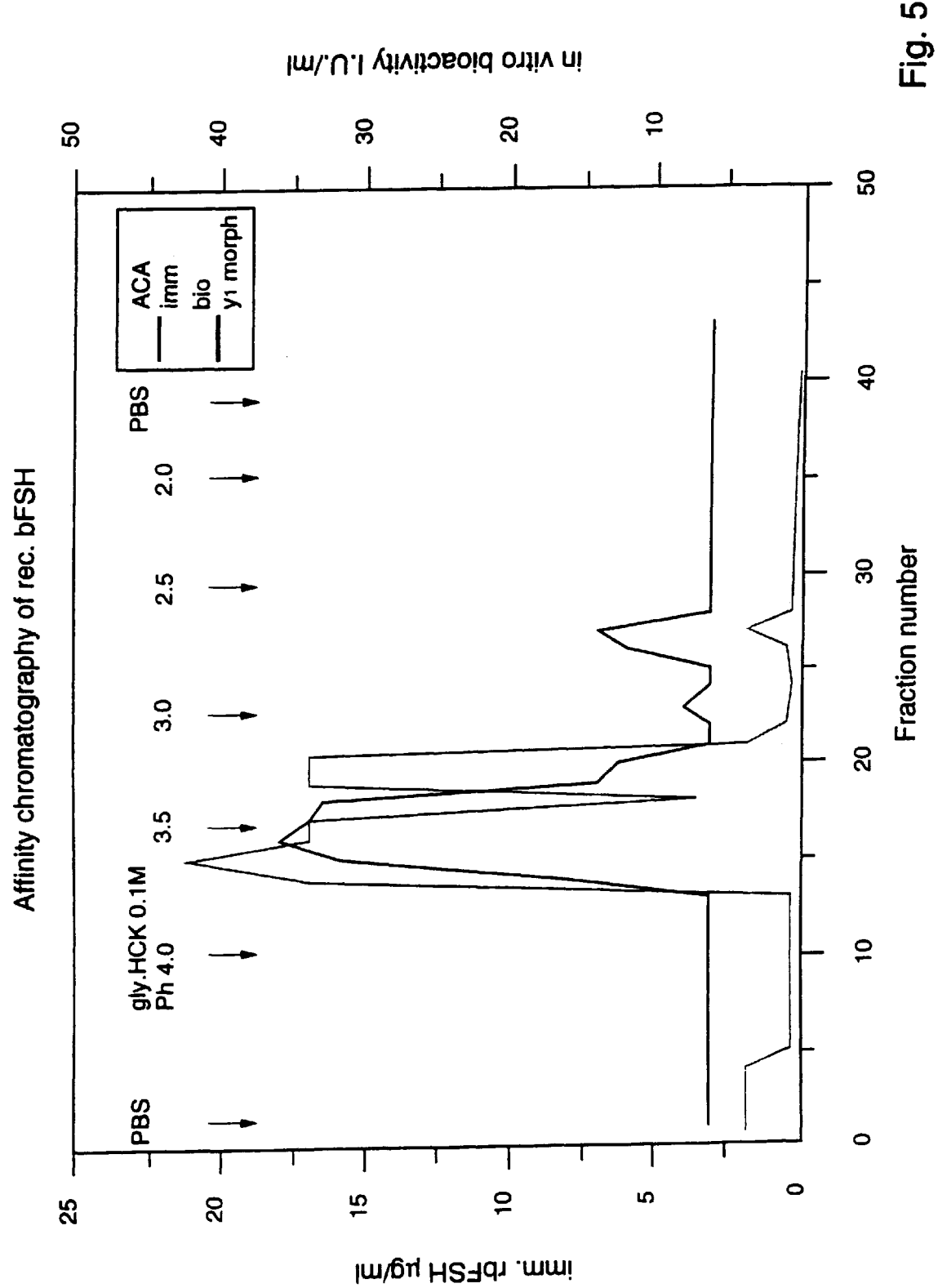
Figure 6:
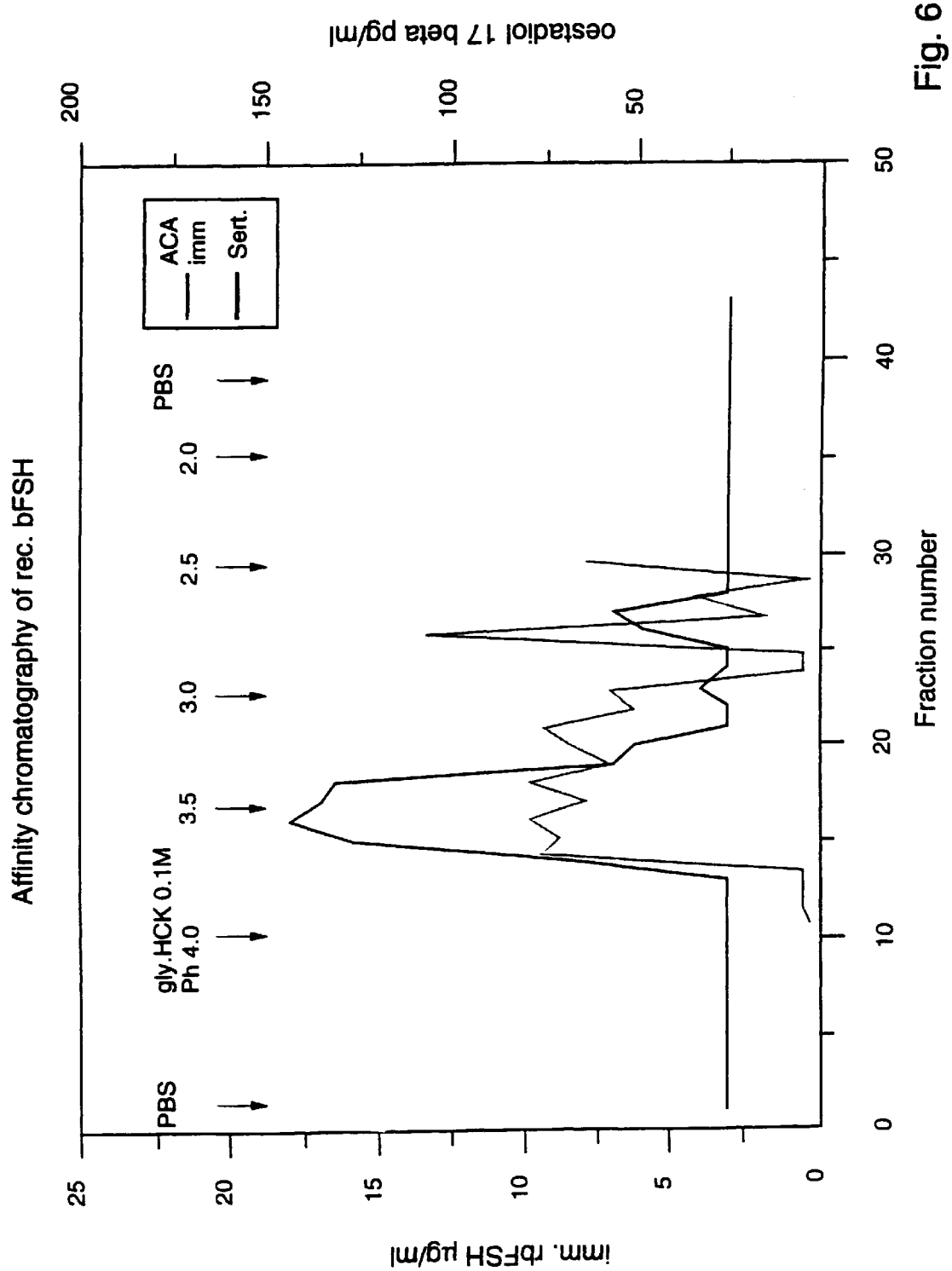

As can be seen from FIGS. 5 and 6, the immunoactivity of the purified rbFSH corresponded fully with the biological activity as measured in the $Y_1$ cell assay and the Sertoli cell assay.

Bioactivity before affinity chromatography was 6.4 or 4.2 IU/ml ($Y_1$ cell assay and Sertoli cell assay, respectively) whereas immunoactivity was 2.5 μg/ml (ACA). Total amount of rbFSH therefore was 833 or 546 IU (bioassay) and 325 μg (immunoassay), respectively. The combined amount of rbFSH of all fractions after affinity chromatography was 25 IU or 50 IU ($Y_1$ cell assay and Sertoli cell assay, respectively), or 23 μg (ACA). Percentage recovery after affinity chromatography therefore was 3.0% ($Y_1$), 9.1% (Sertoli-cell) and 7.1% (ACA), respectively.

Discussion

Production levels of rec.bFSHα and rec.bFSHβ in our system are comparable with gonadotropin subunit levels obtained in the baculosystem which were published previously (Table 1). These levels however are very much dependent on the type of assay and the reference preparation which were used. So far, we have not purified of rbFSH subunits or hormone, and specific (bio)activity per unit of weight is based on ELISA in which purified hormone-subunits were used as reference preparations. It has been mentioned in the literature that specific activity of rhFSH can vary between 10.000 and 40.000 IU mg$^{-1}$, depending on the method of protein recognition and/or the use of various protein standards (Mannaerts et al., 1991).

In our study, specific activity of rbFSH expressed in terms of bFSH (USDA-bFSH-I-2, 854 IU.mg$^{-1}$) bioactivity ($Y_1$ cell assay/cAMP) and bFSH (UCB io58) immunoactivity (ACA) is approximately 20.000 IU.mg$^{-1}$.

More accurate determination of S.A. however awaits further purification of rbFSH and direct estimation of protein content. From these data it will be possible also to calculate the ratio of bioactivity to immunoactivity of rbFSH.

Bioactivity of glycoprotein hormones is dependent also on type and extent of glycosylation as has been demonstrated for rhCGβ (Sridhar and Hasnain, 1993). In order to relate bioactivity of rbFSH to degree and type of glycosation, it will be necessary to analyse glycosidic sidechains of this hormone. This also may reveal possible microheterogeneity, as has been demonstrated for rhFSH (De Boer and Mannaerts, 1990). The observed variation in bioactivity between different bio-assays (cAMP production of $Y_1$ cells, morphological changes of $Y_1$ cells, cAMP production in rat-Sertoli-cells, maturation inhibition of bovine oocytes) (Table 2) may be explained by differences in glycosylation between pituitary and recombinant bFSH.

Until now, bovine recombinant FSH has been produced only in mouse epitheloid cells (Chappel et al., 1988) and in transgenic mice (Greenberg et al., 1991), although reference was made also to CHO cells (Greenberg et al., 1991, commercial preparation from Genzyme Corp.). Reports about application of rbFSH for superovulation in cattle do not give any specification of the rbFSH used (Looney et al., 1988; Wilson et al., 1988; Wilson et al., 1993), although it apparently is from commercial origin.

Most likely all these rbFSH products were based on the same subunit cDNA's as were used in our baculo-expression system. Sofar, the only rFSH which has been produced in the baculovirus system, is human FSH (Lindau-Shepard et al., 1994; Dias et al., 1994). The cDNA that was used for hFSHα subunit consisted of a 51 bp untranslated 5' region, a 72 bp signal sequence, a 276 bp sequence of the a subunit, and a 222 bp untranslated 3' region. In contrast, the cDNA of the β subunit contained the minimal contiguous hFSHβ sequence, including the leader sequence but without untranslated regions at either the 5' or 3' end. It is our feeling that the untranslated 3' region which we have used in the cDNA of the bovine FSHβ subunit, may have contributed to its stability and to a high production level.

To further illustrate this phenomenon the posttranscriptional regulation of bFSHβ subunit mRNA is discussed below FSHβ mRNA The FSHβ subunit is encoded by a single gene in species studied, which has been characterized in the human, rat and cow, and contains three exons and two introns (reviewed by Haisenleder et al. 1994). FSHβ subunit biosynthesis most likely is a rate limiting step in FSH heterodimer assembly and secretion (Greenberg et al., 1991). The FSHβ mRNA nucleotide and polypeptide amino acid sequences are highly conserved between species (approx. 80%). In rats and cows, only one mRNA (of approx. 1.7 kb) has been demonstrated, but the human FSHβ gene produces four mRNA size variations. The different mRNA sizes appear to be due to the use of two different transcription start sites and two different polyadenylation sites, but it is unknown if all four mRNA transcripts are translated or hormonally regulated. The biosynthesis and secretion of LH and FSH are under the control of multiple hormones: GnRH, which is released from the hypothalamus in a pulsatile manner, sex steroid hormones and the gonadal protein hormones inhibin, activin, and follistatin. The latter have preferential effects on FSH; inhibin and follistatin decrease FSHβ mRNA levels and FSH secretion, whereas activin is stimulatory. Follistatin binds activin with high affinity, blocking stimulation of FSH secretion, and inhibin with lower affinity.

Stability of FSHβ mRNA

Inhibin and follistatin appear to repress steady state FSHβ mRNA levels at least in part by reducing the stability of FSHβ transcripts (Dalkin et al., 1993; Carrol et al., 1991). In rats, the pulsatile administration of GnRH stimulates FSHβ gene transcription, while estrogen inhibits FSHβ mRNA transcription in vivo. In contrast, the ability of testosterone to elevate FSHβ mRNA levels in the presence of a GnRH antagonis is independent of any influence on gene transcription, and presumably represents a posttranscriptional effect on FSHβ mRNA stability (reviewed by Haisenleder et al., 1994; Mercer & Chin, 1995). Similarly, the gonadal peptide activin enhances FSHβ mRNA expression in rat pituitary cell cultures, in part by increasing the half-life of the FSHβ transcript over 2-fold (Carrol et al., 1991).

FSHβ mRNA 3'UTR

A common feature of FSHβ genes is an extremely long 3'UTR (1 kb, 1.2 kb and 1.5 kb in the rat, bovine and human genes, respectively). This compares to LHβ- and TSHβ-mRNA which have a total length (including 3'UTR) of approximately 700 bp (Maurer and Beck, 1986).

There are five highly conserved segments within the long 3'UTRs of the rat, human and bovine FSHβ genes. Apart from this observation, sequences within the 3'UTR of several genes have been shown to be important in determining RNA stability (reviewed by Gharib et al., 1990).

Removal of the majority of the 3'UTR from the ovine FSH-β subunit cDNA insert dramatically enhanced the accumulation of oFSHβ-mRNA transcripts in COS cells, indicating a role for this region in regulating mRNA stability. A similar effect is seen in stably transfected CHO cells, although a corresponding effect on oFSHβ mRNA translation is not found, possibly reflecting translational inefficiency of β subunit mRNA (Mountford et al., 1994). The significance of this 3'UTR of FSHβ mRNA is presently unknown, but it has been speculated that it may play a role in determining FSHβ mRNA stability. This is supported by studies showing that elements in the 3'UTR can regulate MRNA in other cell systems (Haisenleder et al., 1994).

AU-rich regions

Of particular interest is the presence of 6 copies of the pentanucleotide AUUUA within the reported 3'-UTR sequence of bovine FSHβ (in the ovine sequence also 6 of such motifs have been found; Mountford et al., 1992). There is compelling evidence to suggest that this element plays a critical role in the destabilization of a number of short-lived cellular mRNAs encoding lymphokines and proto-oncogenes (Cleveland and Yen, 1989). These so-called AU rich sequences, when inserted into 3'UTR of a normally stable mRNA, have a destabilizing effect (Ross, 1988) and cause selective degradation of transiently expressed messengers (Shaw and Kamen, 1986).

These motifs have been found in highly labile mRNAs such a C—fos, or granulocytemonocyte colony-stimulating factor FM—CSF, and resemble the AU-rich motifs in the 3'UTR of the labile human LdhC (testis specific isozyme of lactate dehydrogenase) mRNA (Salehi-Ashtiani & Goldberg, 1995).

Size of FSHβ-mRNAU

Porcine FSHβ subunit CDNA has been used for production of pFSHβ in the baculovirus expression system (Sato et al., 1994, JP930071875). The cDNA used in this system was isolated by Kato (1988) and contained 929 basepairs, although Northern analysis showed a length of about 1.8 kb. The porcine FSHβ gene which was cloned into a baculovirus contained only 436 bp, which consisted of a 18 bp signal sequence, a 327 bp FSHβ gene and a 91 bp 3'UTR (Sato et al., 1994, JP930071875). The total sizes of porcine FSHβ- and FSHβ-mRNA reportedly were in the 2 kb range (Maurer & Beck, 1986). Nucleotide analysis of bovine FSHβ mRNA showed a total length of 1728 basepairs, excluding a several hundred nucleotide tract of poly A at the 3'terminus. Therefore, the 1067 bp 3'UTR of bovine FSH cDNA which we have used (van de Wiel et al., 1995), is approximately ten times as long as the 3'UTR of porcine FSHβ cDNA used by the Japanese group, and is very close to the total length of 1341 bp found by Maurer and Beck (1986). Most importantly it contains four of the six ATTTA sequences found in the full length 3'UTR, whereas the truncated porcine FSHβ 3'UTR described by Sato et al., JP930071875, (1994) contains no ATTTA sequence.

Relationship between size of FSHβ-cDNA and production level

The size of bovine FSHβ mRNA which was isolated and used for expression in the baculovirus system by Sharma, Dighe and Canerall (1993) has not been reported. Production levels of both subunites in the soluble fraction reportedly were approximately 120 ng/ml; no mention was made of production of FSH heterodimer.

Production levels reported for rpFSH in Sf 21 cells by Sato et al., JP930071875 (1994) were approximately 0.1 μg/ml, although in Tn5 cells a production was reported of 1 μg/ml. Specific activity of this rpFSH as calculated from their data was 1250 IU/mg. In our bovine system we obtained production levels of 1–5 μg/ml; specific activity in the same in vitro bioassay as used by Sato et al., JP930071875 (1994) (OMI) was 7700 IU/mg.

As reported in the literature, levels of expression of recombinant proteins in insect cells may be too high, thus compromising posttranslational processing and excretion of the wanted protein into the culture medium (Sridhar et al., 1993; Sridhar & Hasnain, 1993). High production levels of porcine LH receptor for instance resulted in intracellular accumulation and degradation of the product, with relatively low levels excreted into the medium (Bozon et al., 1995; Pajot-Augy et al., 1995). We have now found that increasing the length of the 3'UTR of bFSHβ cDNA which we have used and thus increasing the number of ATTTA sequences, significantly increased the levels of excreted product, as compared to the results of Sato et al., JP930071875 (1994).

Apparently, by selecting the length of the 3'UTR of FSH subunit cDNA, and thus choosing the number of specific ATTTA sequencs, one may selectively modify the stability of the corresponding mRNA, and modify the levels of the product that is excreted by the insect cells used.

REFERENCES

Wilson J. M., K. Moore, A. L. Jones & C. R. Looney. Recombinant bovine follicle-stimulating hormone: dose and duration regimens for superovulation of embryo donors. *Theriogenology* 31 (1989) 1, 273.

Wilson J. M., A. L. Jones, K. Moore, C. R. Looney, K. R. Bondioli.

Superovulation of cattle with a recombinant-DNA bovine follicle stimulating hormone. *Animal Reproduction Science* 33 (1993) 71–82.

Looney C. R., K. R. Bondioli, K. G. Hill & J. M. Massey. Superovulation of donor cows with bovine follicle stimulating hormone (bFSH) produced by recombinant DNA technology. *Theriogenology* 29 (1988) 271.

Esch F. S., A. J. Mason, K. Cooksey, M. Mercado, S. Shimasaki. Cloning and DNA sequence analysis of the cDNA for the precursor of the β chain of bovine follicle stimulating hormone. *Proc. Natl. Acad. Sci. USA* 83 (1986) 6618–6621.

Maurer R. A., A. Beck. Isolation and nucleotide sequence analysis of a cloned cDNA encoding the β subunit of bovine follicle-stimulating hormone. *DNA* 5 (1986) 5, 363–369.

Erwin C. R:, M. L. Croyle, J. E. Donelson, R. A. Maurer.

Nucleotide sequence of cloned complementary deoxyribonucleic acid for the a subunit of bovine pituitary glycoprotein hormones. *Biochemistry* 22 (1983) 4856–4860.

Nilson J. H., A. R. Thomason, M. T. Cserbak, C. L. Moncman, & R. P. Woychik. Nucleotide sequence of a CDNA for the common a subunit of the bovine pituitary glycoprotein hormones. *J. Biol. Chem.* 258 (1983) 4679–4682.

Mountford P. S., M. R. Brandon, T. E. Adams. Expression and characterization opf biologically active ovine FSH from mammalian-cell lines. *J. Molec. Endocr.* 12 (1994) 1, 71–83.

Greenberg N. M., J. W. Anderson, A. J. W. Hsueh, K. Nishimori, J. J. Reeves, D. M. de Avila, D. N. Ward, J. M. Rosen. Expression of biologically active heterodimeric bovine follicle-stimulating hormone in milk of transgenic mice. *Proc. Nat., Acad. Sci. USA.* 88 (1991) 8327–8331.

Chappel S., C. R. Looney & K. R. Bondioli. Bovine FSH produced by recombinant DNA technology. *Theriogenology* 21 (1988) 235.

Greenberg N. M., T. R. Reding, T. Duffy & J. M. Rosen. A heterologous hormone response element enhances suppression of rat beta-casein promoter-driven chloramphenicol acetyltransferase fusion genes in the mammary gland of transgenic mice. *Mol. Endocrinol.* 5 (1991) 10, 1504–1512.

Keene J. L., M. M. Matzuk, T. Otani, B. C. J. M. Fauser, B. Galway, A. J. W. Hsueh, et al. Expression of biologically active human follitropin in Chinese hamster ovary cells. *J. Biol. Chem.* 264 (1989) 4769–4775.

Van Wezenbeek P., J. Draaijer, F. van Meel, W. Olijve. Recombinant follicle-stimulating hormone I. Construction, selection and characterization of a cell line. In: Crommelin D. J. A., H. Schellekens, editors. *From clone to clinic, developments in biotherapy* Vol. I. Kluwer Academic Publishers, Dordrecht, The Netherlands, 1990, pp 245–251.

Hasnain S. E., B. Nakhai, N. Z. Ehtesham, P. Sridhar, A. Ranjan, G. P. Talwar & P. K. Jha. β-subunit of human chorionic gonadotropin hormone and firefly luciferase simultaneously synthesized in insect cells using a recombinant baculovirus are differentially supressed and transported. *DNA and Cell Biology* 13 (1994) 3, 275–282.

King L. A., R. D. Possee. The baculovirus expression system. Chapman and Hall Publ., London, 1992.

Wenyong Chen, Qing-Xiang Shen, Om P. Bahl. Carbohydrate variant of the recombinant βsubunit of human choriogonadotropin expressed in baculovirus expression system. *J. Biol. Chem.* 266 (1991) 7, 4081–4087.

Wenyong Chen, Om P. Bahl. Selenomethionyl analog of recombinant human choriogonadotropin *J. Biol. Chem.* 266 (1991a) 15, 9355–9358.

Wenyong Chen & Om P. Bahl. Recombinant carbohydrates and selenomethionyl variants of human choriogonadotropin. *J. Biol. Chem.* 266 (1991b) 13, 8192–8197.

Sridhar P., S. E. Hasnain. Differential secretion and glycosylation of recombinant human chorionic gonadotropin (βhCG) synthesized using different promoters in the baculovirus expression system. *Gene* 131 (1993.) 261–264.

Sridhar P., A. K. Panda, R. Pal, G. P. Talwar, S. E. Hasnain. Temporal nature of the promoter and not relative strength determines the expression of an extensively processed protein in a baculovirus system. *FEBS* 315 (1993) 3, 282–286.

Jha P. K., R. Pal, B. Nakhai, P. Sridhar & S. E. Hasnain. Simultaneous synthesis of enzymatically active luciferase and biologically active β subunit of human chorionic gonadotropin in caterpillars infected with a recombinant baculovirus. *FEBS* 310 (1990) 2, 148–152.

Nakhai B., R. Pal, P. Sridhar, G. P Talwar & S. E. Hasnain. The a subunit of human chorionic gonadotropin hormone synthesized in insect cells using a baculovirus vector is biologically active. *FEBS* 283 (1991a) 1, 104–108.

Nakhai B., P. Sridhar, R. Pal, G. P. Talwar & S. E. Hasnain. Over-expression and characterization of recombinant beta subunit of the human chorionic gonadotropin hormone synthesized in insect cells infected with a genetically engineered baculovirus. *Indian J. Biochem. Biophysics* 29 (1992) 315–321.

Nakhai B., P. Sridhar, G. P. Talwar & S. E. Hasnain. Construction, purification and characterization of a recombinant baculovirus containing the gene for alpha subunit of human chorionic gonado-tropin. *Indian J. Biochem. Biophysics* 28 (1991b) 237–242.

Huang C. -J., F. -L. Huang, G. -D. Chang, Y. -S. Chang, C. -F. Lo, M. J. Fraser, T. -B. Lo. Expression of two forms of carp gonadotropin a subunit in insect cells by recombinant baculovirus. *Proc. Natl. Acad. Sci. USA.,* 88 (1991) 7486–7490.

Christophe S., P. Robert, S. Maugain, D. Bellet, A. Koman, J. -M. Bidart. Expression of the human follicle-stimulating hormone receptor in the baculovirus system. *Biochem. Biophys. Res. Comm.* 196 (1993) 1, 402–408.

Leung K., A. H. Kaynard, B. P. Negrini, K. E. Kim, R. A. Maurer & T. D. Landefeld. Differential regulation of gonadotropin subunit messenger ribonucleic acids by gonadotropin-releasing hormone pulse frequency in ewes. *Molecular Endocrinology.*1 (1987) 10, 724–728.

Vlak J. M., A. Schouten, M. Usmany, G. J. Belsham, E. C. Klinge-Roode, A. J. Maule, J. W. M. van Lent, D. Zuidema. Expression of cauliflower mosaic virus gene I using a baculovirus vector based upon the p10 gene and a novel selection method. *Virology* 179 (1990) 312–320.

Martens J. W. M., M. M. van Oers, B. van de Bilt, J. M. Vlak & P. Oudshoorn. Efficient recovery and screening of baculovirus p10-based recombinants. 1994 (submitted).

Van Rijn P. A., R. G. P. van Gennip, E. J. de Meijer & R. J. M. Moormann. A preliminary map of epitopes on envelope glycoprotein $E_1$ of HCV strain Brescia. *Veterinary Microbiology* 33 (1992) 221–230.

Sambrook J., E. F. Fritsch & T. Maniatis. Molecular cloning: a laboratory manual, 2nd ed. Cold Spring Harbor Laboratory, Cold Spring Harbor, N.Y., 1989.

Summers M. & G. Smith. A manual of methods for baculovirus vectors and insect culture procedures. *Tex. Agric. Exp. Stn. Bull.* 1555. College Station, Tex. 1987.

Wensvoort G., C. Terpstra, J. Boonstra, M. Bloemraad, D. van Zaane. Production of monoclonal antibodies against swine fever virus and their use in laboratory diagnosis. *Vet. Microbiol.* 12 (1986) 101–108.

Hulst M. M., D. F. Westra, G. Wensvoort, R. J. M. Moormann. Glycoprotein $E_1$ of hog cholera virus expressed in insect cells protects swine from hog cholera. *J. Virology* 67 (1993) 9, 5435–5442.

Wensvoort G., M. Bloemraad & C. Terpstra. An enzyme immunoassay employing monoclonal antibodies and detecting specifically antibodies to classical swine fever virus. *Vet. Microbiol.* 17 (1988) 129–140.

Belyaev A. S. & P. Roy. Development of baculovirus triple and quadruple expression vectors: co-expression of three or four bluetongue virus proteins and the synthesis of bluetongue virus-like particles in insect cells. *Nucleic Acids Research* 21 (1993) 5, 1219–1223.

French T. J., J. J. A. Marshall & P. Roy. *J. Virol.* 64 (1990) 5695–5700.

Lindau-Shepard B., K. E. Roth, J. A. Dias. Identification of amino acids in the c-terminal region of human follicle-stimulating hormone (FSH) β-subunit involved in binding to human FSH receptor. *Endocrinology* 135 (1994) 1235–1240.

Wu J. B., P. G. Stanton, D. M. Robertson and M. T. W. Hearn. Isolation of FSH from bovine pituitary glands. *J. Endocrinoloqy* 137 (1993) 59–68.

De Boer W., and B. Mannaerts. Recombinant human follicle stimulating hormone. II. biochemical and biological characteristics. In: D. J. A. Crommelin and H. Schellekens (eds.), From clone to clinic, Developments in biotherapy, Vol I, Kluwer Academic Publ., Dordrecht, The Netherlands, 1990, pp 253–259.

Geysen H. M., R. H. Meloen, S. J. Barteling. Use of peptide synthesis to probe viral antigens for epitopes to a resolution of a single amino acid. *Proc. Natl. Acad. Sci. USA* 81 (1984) 3998–4002.

Westhoff W. E., J. W. Slootstra, W. C. Puijk, D. Kuperus, J. F. Flinterman, H. B. Oonk and R.H. Meloen. Detection of immuno-dominant epitopes on follicle-stimulating hormone. 1994, submitted for publication.

Vlak J. M. and van Oers M. M. (1994). Personal communication. Oonk R. B., J. A. Grootegoed and H. J. van der Molen. Comparison of the effects of insulin and follitropin on glucose metabolism by Sertoli cells from immature rats. *Molecular and Cellular Endocrinology* 42 (1985) 39–48.

Oonk R. B. and J. A. Grootegoed. Identification of insulin receptors on rat Sertoli cells. *Molecular and Cellular Endocrinology* 49 (1987) 51–62

Dias J. A, Yiqiu Zhang, Xunzian Liu. Receptor binding and functional properties of chimaeric human follitropin prepared by an exchange between a small hydrophilic intercysteine loop of human follitropin and human lutropin. *J. Biol. Chem.* 269, 41 (1994) 25289–25294.

Roth K. E., Cheng Liu, B. A. Shepard, J. B. Shaffer, J. A. Dias. The flanking amino acids of the human follitropin β-subunit 33–53 region are involved in assembly of the follitropin heterodimer. *Endocrinology* 132 (1993) 2571–2577.

Haisenleder D. J., Dalkin A. C., Marshall J. C. Regulation of gonadotropin gene expression.

In: The Physiology of Reproduction, E. Knobil & J. D. Neill eds., Raven Press Ltd., New York 1994, Chapter 31, pp. 1793–1831.

Dalkin A. C., Knight C. K., Shupnik M. A., Haisenleder D. J., Aloe J., Kirk S. E., Yasin N., Marshall J. C. Ovariectomy and inhibin immunoneutralization acutely increase follicle stimulating hormone-• messenger ribonucleic acid concentrations: evidence for a nontranscriptional mechanism. Endocrinology 132 (1993) 1297–1304.

Carrol R. S., Corrigan A. Z., Vale W., Chin W. W. Activia stabilizes follicle-stimulating hormone-beta messenger ribonucleic acid levels. Endocrinolgy 129 (1991) 1721–1726.

Mercer J. E., Chin W. W. Regulation of pituitary gonadotrophin gene expression. Human Reproduction Update 1 (1995) 4, 363–384.

Gharib S. D., Wierman M. E., Shupnik M. A., Chin W. W. Molecular biology of the pituitary gonadotrophins. Endocrine Reviews 11 (1990) 1, 177–199.

Mountford P. S., Brandon M. R., Adams T. E. Removal of 3' untranslated sequences dramatically enhances transient expression of ovine follicle-stimulating hormone beta gene messenger ribonucleic acid. J. Neuroendocrinology 4 (1992) 6, 655–658.

Cleveland D. W., Yen T. J. Multiple determinants of eukaryotic mRNA stability. New Biol. 1 (1989) 121–126. Ross J. Messenger RNA Turnover in Eukaryotic Cells. Mol. Biol. Med. 5 (1988) 1–14.

Shaw G., Kamen R. A conserved AU sequence from the 3' untranslated region of GM—CSF mRNA mediates selective mRNA degradation. Cell 46 (1986) 659–667.

Salehi-Ashtiani K., Goldberg E. Posttranscriptional regulation of primate Ldhc MRNA by its AUUUA-like elements. Molecular Endocrinology 9 (1995) 12, 1782–1790.

Sato, Ihara, Kato Y., Mori, Ueta, Honda. Swine FSH (follicle stimulating hormone) expressed by baculovirus and method of manufacturing the same. Patent application (1994) 6-121687.

Kato Y. Cloning and DNA sequence analysis of the CDNA for the precursor of porcine follicle stimulating hormone (FSH) • subunit. Molecular and Cellular Endocrinology 55 (1988) 107–112

Van de Wiel D. F. M., Van Rijn P. A., Meloen R. H. and Moormann R. J. M. Production of biologically active recombinant bovine follicle stimulating hormone in the baculovirus expression system. (1995, submitted).

Sharma S. C., Dighe R.., Canerall J. F. Expression of bovine alpha and beta follicle stimulating hormone in baculovirus. Molecular Biology of the Cell 4 (1993) 136$^a$ (Abstr. #791).

Roth K. E., Lin D., Shepard B. A., Shaffer J. B., Dias J. A. The flanking amino acids of the human follitropin •-subunit 33–53 region are invloved in assembly of the follitripin heterodimer. Endocrinology 132 (1993) 6, 2571–2577.

Bozon V., Remy J. J., Pajot-Augy E., Couture L., Biache G. Severini M., Salesse R. Influence of promoter and signal peptide on the expression and secretion of recombinant porcine LH extracellular domain in baculovirus/ lepidopteran cells or the caterpillar system. J. Molec. Endocrinol. 14 (1995) 277–284.

Pajot-Augy E., Couture L., Bozon V., Remy J. J., Biache G., Severini M., Huet J. C., Pernollet J. C., Salesse R. High-level expression of recombinant porcine LH receptor in baculovirus-infected insect cells or caterpillars. J. Molec. Endocrinol. 14 (1995) 51–66.

TABLE 1

Comparison of production of recombinant gonadotropic hormone (subunit) according to published data

| literature reference | expression system | matrix | rec. expression product | max. prod. $\mu g \cdot ml^{-1} \cdot 24\ h^{-1}$ | method |
|---|---|---|---|---|---|
| Chappel | '88 C127 mouse epitheloid cells | | rbFSHαβ | | |
| Keene | '89 CHO cells | αMEM | rhFSHαβ | 0.5 | G.C. aromatase assay |
| v. Weezenbeek | '90 CHO cells | medium | rhFSHαβ | 84* | Steelman Pohley |
| Greenberg | '91 transgenic mice | milk | rhFSHαβ | 2500 15.3* | RIA RRA |
| Chen, Shen & Bahl | '91 baculo | Grace medium | rhCGβ | 1.5 | RIA |
| Chen & Bahl | '91 baculo | Grace medium | rhCGαβ | | RIA |
| Huang | '91 baculo | TNM-FH medium | r carp GTHα | 4.5 | RIA |
| Nakai, Sridhar, Talwar, Hasnain | '91 baculo | medium | rhCGα | 11.3 | RIA |
| Nakhai' | '91 baculo | medium | rhCGα | 11.3 | RIA |
| Nakhai | '92 baculo | medium | rhCGβ | 8.02 | RIA |

TABLE 1-continued

Comparison of production of recombinant gonadotropic hormone (subunit) according to published data

| | | | | | | |
|---|---|---|---|---|---|---|
| Jha | '92 | baculo | larva body tissue | rhCGβ | 1.2[c] | RIA |
| | | | hemo-lymph | | 1.4[o] | RIA |
| Sridhar | '93 | baculo | medium | rhCGβ | 11.3 | RIA |
| Roth | '93 | CHO cells | D-MEM | rhFSHαβ | 1.0 | RIA |
| Sridhar & Hasnain | '93 | baculo | medium | rhCGβ | | Western blot |
| Hasnain | '94 | baculo | medium | rhCGβ | 8.55 | RIA |
| Mountford | '94 | CHO cells | α-MEM | roFSHαβ | 0.062 | RRA |
| Dias | '94 | baculo | TNM-FH | rhFSHαβ | 8–10 | RIA/ELISA |
| Lindau-S. | '94 | baculo | Grace medium | rhFSHαβ | 1–2 | ELISA |
| v.d. Wiel (this report) | '94 | baculo | Sf900 medium | rbFSHαβ | 1–5 | ELISA |

| ref. prep | max. prod. IU · ml$^{-1}$ · 24 h$^{-1}$ | method | ref. prep | remarks |
|---|---|---|---|---|
| | | G.C./prog Steelman-Pohley | USDA-FSH | |
| hFSH-LER-907 | 1.1 | G.C. aromatase assay | hFSH-LER-907 | |
| urinary FSH/hMG | 650 | Steelman-Pohley | urinary FSH/hMG | continuous perfusion system *FSH/hMG 7778 IU · mg$^{-1}$ |
| USDA-B5 | 67 | RRA | NIH-FSH-S9 | *NIH-FSH-S9: 4000 IU · mg$^{-1}$ |
| NIH-FSH-S9 | 66 | G.C./E$_2$ | NIH-FSH-S9 | |
| hCGβ | | RRA Leydig cell/cAMP/prog. | hCGαβ | |
| | | RRA Leydig cell/cAMP/prog. | hCGαβ | |
| pituitary carp GTHα | | carp testis/T | pituitary carp GTHα | |
| hCGα | | RRA Leydig cell/T | | |
| hCGα | 2[b] | RRA Leydig cell/T | hCGαβ | [b]calculated on hCG: 10.000 IU · mg$^{-1}$ |
| hCGβ | 17[b] | RRA | hCGαβ | |
| | 13[b] | Leydig cell/T | hCGαβ | |
| hCGβ | 6[b,d] | Leydig cells/T | hCGαβ | [c]after 96 hrs [d]per larva |
| hCGβ | 2[b,d] | Leydig cells/T | hCGαβ | |
| hCGβ | 90[b] | Leydig cells/T | hCGαβ | |
| | | RRA | hCGαβ | |
| pituary hFSH | | RRA | pituary hFSH | |
| hCGβ | | | | |
| hCGβ | 18[b] | RRA | hCGαβ | |
| | 13[b] | Leydig cell/T | hCGαβ | |
| NIDDK-oFSH-RP-1 | 0.02 | RRA | NIDDK-oFSH-RP-1 | NIDDK-oFSH-RP-1:20 U · mg$^{-1}$ |
| | 0.03 | Sertoli cell/E2 | | |
| pituitary hFSH | | RRA Y$_1$ cell assay | pituitary hFSH | |
| pituitary FSH | | RRA Y$_1$ cell/cAMP | pituitary FSH | |
| bFSH-iO28 | 20 | Y$_1$ cell/cAMP | USDA-bFSH-1-2 | USDA-bFSH-I-2:854 IU · mg$^{-1}$ |

Abbreviations are:
b = bovine
h = human
o = ovine
G.C. = granulosa cell
prog. = progesterone
arom. = aromatase
hCG = human chorionic gonadotrophin
RRA = radio receptor assay
E2 = oestradiol-17β
T = testosterone

TABLE 2

Production level[1] (IU/ml for bioassays, and μg/ml for ACA and specific activity[2] (IU/μg) of rbFSH

| assay | batch 1/7/94 |
|---|---|
| $Y_1$ morphol[3] | 8.54 8.54 8.54 4.27 |
| x ± S.D. | 7.47 ± 2.14 |
| S.A. | 2.49 |
| $Y_1$ cAMP[4] | 19.1 29.9 23.9 |
| x ± S.D | 24.3 ± 5.41 |
| S.A | 8.1 |
| Sertoli cell[4] | 13.7 4.4 2.7 |
| x ± S.D. | 6.90 ± 4.83 |
| S.A. | 2.3 |
| OMI | 15.0 31.0 |
| x ± S.D. | 23.0 ± 11.3 |
| S.A. | 7.7 |
| ACA | 1.8 1.6 5.6 |
| x ± S.D. | 3.0 ± 1.8 |

[1] harvest at 72 hours after infection (p.i.), except when indicated

[2] $S.A. \frac{IU/ml \ (biossay)}{\mu g/ml \ (ACA)}$

[3] measurement of change in cell morphology

[4] measurement of cAMP (½ max. level), except when indicated.

---

What is claimed is:

1. A method for producing bovine follicle stimulating hormone, said method comprising:

introducing a first nucleic acid encoding an alpha subunit and a second nucleic acid encoding a beta subunit of bovine follicle stimulating hormone into an insect cell by means of at least one vector based on a baculovirus wherein at least one of said first and second nucleic acids contains at least one ATTTA sequence having a destabilizing effect on mRNA in a stretch of untranslated nucleotides at the at least one of said first and second nucleic acid's 3' end, culturing said resulting insect cell in a suitable medium thus producing bovine follicle stimulating hormone, and recovering said thus produced bovine follicle stimulating hormone from said cultured medium.

2. Recombinant bovine follicle stimulating hormone obtainable by a method according to claim 1 having a biological activity of a least 8000 I.U./mg in a $Y_1$ cell assay.

3. A method of treating super-ovulation or reproductive problems in a mammal, the method comprising administering recombinant bovine follicle stimulating hormone according to claim 2 to said mammal.

4. A pharmaceutical preparation comprising recombinant bovine follicle stimulating hormone according to claim 2.

5. A method of conducting in vitro oocyte-maturation and fertilization comprising contacting an oocyte with recombinant bovine follicle stimulating hormone according to claim 2.

6. A recombinant Baculovirus vector or a recombinant Baculovirus comprising at least a nucleic acid coding for the alpha subunit of bovine follicle stimulating hormone wherein said encoding nucleic acid comprises at least one ATTTA sequence having a destabilizing effect on mRNA, in a stretch of untranslated nucleotides at the nucleic acid's 3' end.

7. A vector or a baculovirus according to claim 6, comprising nucleic acid encoding the alpha and beta subunits of bovine follicle stimulating hormone.

8. An insect cell comprising a vector and/or baculovirus according to claim 7.

9. An insect cell comprising a vector and/or baculovirus according to claim 6.

10. A method for producing bovine follicle stimulating hormone, said bovine follicle stimulating hormone having bioactivity in an in vitro bioassay comprising culturing an insect cell according to claim 9 in a suitable medium and harvesting the bovine follicle stimulating hormone from the cultured medium.

11. The recombinant Baculovirus vector or recombinant Baculovirus of claim 6 comprising nucleic acid encoding the alpha and beta subunits of bovine follicle stimulating hormone.

12. An insect cell comprising a vector and/or baculovirus according to claim 11.

13. An insect cell comprising a vector and/or baculovirus according to claim 6.

14. A recombinant Baculovirus vector or a recombinant Baculovirus comprising at least a nucleic acid coding for the beta subunit of bovine follicle stimulating hormone wherein said encoding nucleic acid comprises at least one ATTTA sequence having a destabilizing effect on mRNA, in a stretch of untranslated nucleotides at the nucleic acid's 3' end.

15. The recombinant Baculovirus vector or recombinant Baculovirus of claim 14 comprising nucleic acid encoding the alpha and beta subunits of bovine follicle stimulating hormone.

16. An insect cell comprising a vector and/or baculovirus according to claim 15.

17. An insect cell comprising a vector and/or baculovirus according to claim 14.

* * * * *

UNITED STATES PATENT AND TRADEMARK OFFICE
CERTIFICATE OF CORRECTION

PATENT NO. : 6,183,987 B1
DATED : February 6, 2001
INVENTOR(S) : Dirk Franciscus Marinus van de Wiel et al.

It is certified that error appears in the above-identified patent and that said Letters Patent is hereby corrected as shown below:

Title page, Item [54] and Column 1, line 3,
Change "STIMULATION" to -- STIMULATING --

Title page,
Item [73], Assignee, change "Diergezonheld" to -- Diergezonheid --

Column 2,
Line 19, delete the period after "insect"
Lines 34-58, delete the lines in their entirety and insert therefor, centered on its own line, -- SUMMARY OF THE INVENTION --

Column 3,
Line 62, change "DRAWING" to -- DRAWINGS --
Line 66, change "ACNPV" to -- AcNPV --

Column 4,
Line 3, change "Pa" to -- P, --
Line 5, change "$E_1$" to -- E1 -- and change "E1" to -- $E_1$ --
Line 8, change "immuno" to -- immune --

Column 5,
Line 60, change "pARKh1" to -- $pARKh_1$ --

Column 7,
Line 30, change "Radiolabelina" to -- Radiolabeling --

Column 10,
Line 12, after "AFP" delete "0"
Line 54, change "024" to -- 24 --

Column 13,
Line 57, change "subunites" to -- subunits --

Column 14,
Line 16, change "sequencs" to -- sequences --
Lines 44 and 48, change "a" to -- α --
Line 48, change "CDNA" to -- cDNA --
Line 52, change "opf" to -- of --

Column 15,
Lines 44 and 61, change "a" to -- α --

Column 16,
Line 5, delete the period after "*Endocrinology*"

UNITED STATES PATENT AND TRADEMARK OFFICE
CERTIFICATE OF CORRECTION

PATENT NO. : 6,183,987 B1
DATED : February 6, 2001
INVENTOR(S) : Dirk Franciscus Marinus van de Wiel et al.

It is certified that error appears in the above-identified patent and that said Letters Patent is hereby corrected as shown below:

<u>Column 18,</u>
Line 9, change "MRNA" to -- mRNA --
Line 16, change "CDNA" to -- cDNA --

Signed and Sealed this

Thirtieth Day of September, 2003

JAMES E. ROGAN
*Director of the United States Patent and Trademark Office*

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 37 base pairs
      (B) TYPE: nucleic acid
      (C) STRANDEDNESS: unknown
      (D) TOPOLOGY: unknown (ii) MOLECULE TYPE: other nucleic acid (iii) HYPOTHETICAL: NO (xi) SEQUENCE DESCRIPTION: SEQ ID NO: 1:

GAGGGATCCA GATCTAGAGG ATTTAGGTGA CACTATA    37

(2) INFORMATION FOR SEQ ID NO: 2:

(i) SEQUENCE CHARACTERISTICS:
      (A) LENGTH: 35 base pairs
      (B) TYPE: nucleic acid
      (C) STRANDEDNESS: unknown
      (D) TOPOLOGY: unknown (ii) MOLECULE TYPE: other nucleic acid (iii) HYPOTHETICAL: NO (xi) SEQUENCE DESCRIPTION: SEQ ID NO: 2:

CCTGAGAGAT CTATCATGAA GTCTGTCCAG TTCTG    35

(2) INFORMATION FOR SEQ ID NO: 3:

(i) SEQUENCE CHARACTERISTICS:
      (A) LENGTH: 19 base pairs

```
        (B) TYPE: nucleic acid
        (C) STRANDEDNESS: unknown
        (D) TOPOLOGY: unknown (ii) MOLECULE TYPE: other nucleic acid (iii) HYPOTHETICAL: NO (xi) SEQUENCE DESCRIPTION: SEQ ID NO: 3:

CAACCCAACA CAATATATT                                                        19

(2) INFORMATION FOR SEQ ID NO: 4:

(i) SEQUENCE CHARACTERISTICS:
        (A) LENGTH: 21 base pairs
        (B) TYPE: nucleic acid
        (C) STRANDEDNESS: unknown
        (D) TOPOLOGY: unknown (ii) MOLECULE TYPE: other nucleic acid (iii) HYPOTHETICAL: NO (xi) SEQUENCE DESCRIPTION: SEQ ID NO: 4:

GGTTACAAAT AAAGCAATAG C                                                     21
```